US006875451B2

(12) United States Patent
Ellison et al.

(10) Patent No.: US 6,875,451 B2
(45) Date of Patent: Apr. 5, 2005

(54) COMPOSITIONS AND METHODS FOR THE TREATMENT OF PRIMARY AND METASTATIC NEOPLASTIC DISEASES USING ARSENIC COMPOUNDS

(75) Inventors: Ralph M. Ellison, Palm Beach, FL (US); Fred H. Mermelstein, Upper Montclair, NJ (US)

(73) Assignee: PolaRx Biopharmaceuticals Inc., New York, NY (US)

( * ) Notice: Subject to any disclaimer, the term of this patent is extended or adjusted under 35 U.S.C. 154(b) by 0 days.

(21) Appl. No.: 09/173,531

(22) Filed: Oct. 15, 1998

(65) Prior Publication Data

US 2002/0183385 A1 Dec. 5, 2002

Related U.S. Application Data

(60) Provisional application No. 60/062,375, filed on Oct. 15, 1997.

(51) Int. Cl.[7] .......................... A61K 33/36; A61K 9/00; A61K 31/282; A61K 31/33; A61K 33/42
(52) U.S. Cl. ....................... 424/623; 424/422; 424/620; 424/629; 424/649; 424/184.1; 424/277.1; 514/2; 514/8; 514/12; 514/21; 514/23; 514/25; 514/28; 514/29; 514/31; 514/34; 514/45; 514/49; 514/90; 514/110; 514/171; 514/183; 514/184; 514/185; 514/249; 514/274; 514/283; 514/444; 514/449; 514/492; 514/504; 514/588; 514/615; 514/733; 514/908
(58) Field of Search ................................ 424/422, 620, 424/623, 624–629, 649, 184.1, 277.1, 621, 622; 514/2, 8, 12, 21, 23, 25, 28, 29, 31, 34, 45, 49, 90, 110, 171, 183, 184, 185, 249, 274, 283, 444, 449, 492, 504, 588, 615, 733, 908

(56) References Cited

U.S. PATENT DOCUMENTS

| 132,275 A | 10/1872 | Gettings ..................... 424/620 |
| 232,807 A | 10/1880 | Dennett ........................ 514/25 |
| 3,700,498 A | 10/1972 | Kanazawa et al. .......... 430/128 |
| 4,497,780 A | 2/1985 | Barin et al. .................... 423/88 |
| 5,759,837 A | 6/1998 | Kuhajda et al. ............. 435/193 |

FOREIGN PATENT DOCUMENTS

| CN | 1061908 A | 6/1992 |
| CN | 1079391 A | 12/1993 |
| CN | 1081104 A | 1/1994 |
| CN | 1119113 A | 3/1996 |
| CN | 1121807 A | 5/1996 |
| CN | 1122700 A | 5/1996 |
| CN | 1131037 A | 9/1996 |
| CN | 1133725 A | 10/1996 |
| JP | 51-88620 | 3/1976 |
| WO | WO 94/02108 | 2/1994 |
| WO | WO 95/01789 | 1/1995 |
| WO | WO 95/22336 | 8/1995 |

OTHER PUBLICATIONS

Rosner, S., "Immunological enhancement of chemotherapy in advanced brain cancer," Acta Neurologica Latinoamericana, vol. 21(1–4), pp. 126–132 (1975).*

Repetto, G. et al., "Comparatice in vitro effects of sodium arsenite and sodium arsenate on neuroblastoma cells," Toxicology, vol. 92(1–3), pp. 143–153 (1994).*

Shimotsuura, S., "Studies on the antineoplasmic actions of As2O3," Shikwa Gakuho, vol. 86, pp. 1237–1253, 1986.*

Shen, Zhi–Xiang et al., "Use of arsenic trioxide (As2O3) in the treatment of Acute Promyelocytic Leukemia ... " Blood, vol. 89(9), pp. 3354–3360, May 1997.*

Chen, Guo–Qiang et al., "In vitro studies on cellular and molecular mechanisms of arsenic trioxide (As2O3) in the treatment of Acute Promyelocytic leukemia ... " Blood, vol. 88(3), pp. 1052–1061, Aug. 1996.*

Zhu, Jun et al., "Arsenic–induced PML targeting onto nuclear bodies: Implications for the treatment of acute promyelocytic leukemia," Proc. Natl. Acad. Sci., vol. 94, pp. 3978–3983, Apr. 1997.*

Sun, Hongde et al., "32 cases of acute early granulocytic leukemia treated with Al–Ling No. 1 in combination with Chinese medical practice of pattern identification," Zhongguo Zhongxiyi Jiehe Zazhi, vol. 12(3), pp. 170–171, 1992.*

Peng, Zhang et al., "Treatment of acute promyelocytic leukemia with intravenous arsenic trioxide," Chinese Journal of Hematology, vol. 17, Translation, Feb. 1996.*

International Search Report (Jul. 2004).

Kunio Kitamura et al., "New Retinoids and arsenic compounds for the treatment of refractory acute promyelocylic leukemia: clinical and basic studies for the next generation", Cancer Chemother Pharmacol, (1977), 40 (Suppl) pp. S36–S41.

Zhu Chen et al., "Acute Promyelocytic Leukemia: Cellular and Molecular Basis of Differentiation and Apoptosis", Pharmacol. Ther., vol. 76, Nos. 1–3, pp. 141–149, 1997.

(Continued)

*Primary Examiner*—John Pak
(74) *Attorney, Agent, or Firm*—Foley & Lardner LLP

(57) ABSTRACT

The invention relates to the use of arsenic compounds to treat a variety of neoplastic diseases. The present invention encompasses the administration to a mammal of arsenic in the form of a salt, complex, organic compound or ionic solution to treat tumors of epithelial tissue, connective tissue, central nervous system, lymphoid tissue, hematopoietic cells and tumors associated with oncogenic viruses. This invention also encompasses the treatment of hematopoietic disorders in mammals by the administration of one or more arsenic compounds to said mammal. Further, the arsenic compounds may be used to treat metastatic neoplastic diseases.

11 Claims, 10 Drawing Sheets

OTHER PUBLICATIONS

Database Medline Online! US National Library of Medicine (NLM), Bethesday, MD US; Aug. 25, 1997, Melino G. et al., "Retinoic acid receptors alpha and gamma mediate the induction of "tissue" transglutaminase activity and apoptosis in human neuroblastoma cells", XP002284763, Database accession No. NLM9281352 *ABSTRACT.

Database Medline Online! US National Library of Medicine (NLM) Bethesda, MD, US; Jul. 1997, Cooper M. P. et al., "All–trans retinoic acid induced gene expression and growth inhibition in head and neck cancer cell lines" XP002284764 Database accession No. NLM9307717 *ABSTRACT & Oral Oncology, Jul. 1997, vol. 33, No. 4, pp. 270–274, ISSN: 1368–8375.

International Search Report for EP 03019594 (Nov. 4, 2003).

Matthew Block et al., "Biological Studies with Arsenic IV. The Histopathologic Effect of Arsenic Upon the Hematopoietic Tissues of Patients with Leukemia", The Journal of Laboratory and Clinical Medicine, vol. 41, No. 4, Apr. 1953, pp. 499–515.

P. Rousellot et al., "Arsenic derivatives: Old drugs for new indications!, Les Derives Arsenicaux: De Vieux Medicaments Pour Des Indications Renouvelees",Hematologie, vol. 4, No. 3, May 1998, pp. 95–97.

P. Rousellot et al., "Arsenic trioxide (AS2O3) and Metarsoprol induce myeloma cell apoptosis in vitro with a preferential effect on tumoral cells in patients' bone marrow", Blood, vol. 90, No. 10, Nov. 15, 1997, p. 325A.

Z. Xie et al., "Metasoprol and arsenic trioxide increase cell death on doxorubicin–resistant human leukemia and myeloma cells by regulating expression of BCL–2 apoptosis regulatory family", BLOOD, vol. 90, No. 10, Nov. 15, 1997, pp. 495 A.

DATABASE EPODOC 'Online! European Patent Office, the Hauge, NL., CN1180563, May 16, 1998, Zhao Qingtuan: XP002260136 *abstract*.

International Search Report for EP 03019595 (Oct. 24, 2003).

Edward B. Silberstein, "Radionuclide Therapy of Hematologic Disorders", Seminars in Nuclear Medicine, vol. 9, No. 2, Apr. 1979, pp. 100–107.

David A. Sears MD, "History of the Treatment of Chronic Myelocytic Leukemia", American Journal of the Medical Sciences, vol. 296, No. 2, Aug. 1988, pp. 85–86.

Zhi–Xiang Shen et al., "Use of Arsenic Trioxide ($As_2O_3$) in the Treatment of Acute Promyelocytic Leukemia (APL); II. Clinical Efficacy and Pharmacokinetics in Relapsed Patients", Blood, vol. 89, No. 9, May 1997, pp. 3354–3360.

International Search Report for EP Application No. 03019628 (Oct. 27, 2003).

W. Zhang et al., "The induction of apoptosis and cell cycle arrest by arsenic trioxide in lymphoid neoplasms", Leukemia (1998), vol. 12, No. 9, Sep. 1998, pp. 1383–1391.

John G. Kidd, "Effects of Arsenic Azoproteins on Mouse Lymphoma Cells in Vivo* With Observations on the Effects of Other "Anti–Lymphoma" Agents and On the Susceptibility to these Effects of Lymphoma Cells of Various Types", Journal of Experimental Medicine, vol. 108, 1958, pp. 665–684.

Jacques Debray, "Treatment of Hodgkin's Disease", Therapie, vol. 9, 1954, pp. 106–118.

G. Lotti, "Abandonment of arsenic in medical therapy of malignant granuloma (Hodgkin's disease): is it justified?!" Revue Medicale Du Moyen–Orient, vol. 24, No. 2, Mar. 1967 pp. 110–111.

International Search Report for EP 03029713 (Mar. 31, 2004).

D.A. Sears, "History of the Treatment of Chronic Myelocytic Leukemia", American Journal of Medical Sciences, vol. 296, No. 2, Aug. 1988, pp. 85–86.

Y.L. Kwong et al., "Delicious Poison: Arsenic Trioxide for the Treatment of Leukemia", Blood, vol. 89, No. 9, May 1997, pp. 3487–3488.

Sun et al., "Ai Ling #1 and Traditional Chinese Medicine in the Treatment of 32 Patients with Acute Promyelocytic Leukemia," Chinese J of Traditional Chinese and Western Medicine, pp. 170–171, vol. 12, No. 3, 1992.

"Arsen (III)–Sulfid $As_2S_2$", Gmelin's Arsenic, 8th. Edition, 17: 422–433, 1952.

"Goodman & Gilman's The pharmacological basis of therapeutics", ninth edition, McGraw–Hill, Health Professions Division, pp. 1659–1662 (Date not Known).

"Inorganic Arsenic Compounds Other Than Arsine Health and Safety Guide, Health and Safety Guide No. 70", WHO, Geneva, 1992.

Akao et al., "Arsenic Induces Apoptosis in B–cell Leukemic Cell Lines in Vitro: Activation of Caspases and Down–regulation of Bcl–2 Protein", British J of Hematology, 102. 1055–1060, 1998.

Andre et al., "The PML and PML/RARα Domains: from autoimmunity to molecular oncology and from retinoic acid to arsenic", Experimental Cell Research, 229: 253–260, 1996.

Arsenic, Environmental Health Criteria 18, Geneva: WHO, 1981.

Chemical Abstract, 63–Pharmaceuticals 11:317, #111: 219272j and 111: 219276p, 1987–1991.

Chen et al., "In vitro studies on cellular and molecular mechanisms of arsenic trioxide ($As_2O_3$) in the treatment of acute promyelocytic Leukemia: $As_2O_3$ induces $NB_4$ cell apoptosis with down regulation of Bcl–2 expression and modulation of PML–RARα/PML proteins", Blood 88(3):1052–1061, 1996.

Chen et al., "Use of Arsenic Trioxide ($As_2O_3$) in the Treatment of Acute Promyelocytic Leukemia (APL): I. $As_2O_3$ Exerts Dose–Dependent Dual Effects on APL Cells", Blood 89(9):3345–3353, 1997.

Chung et al., "Influence for Carcinoma Cell and Lymphatic cell of Acetyl Arsonate", Yakhak Hoeji 40(5):599–607, 1996.

Cutler et al., Article IV, American Journal of the Medical Sciences, pp. 74–84.

Cuzick et al., "Medicinal arsenic and internal malignancies", Br. J. Cancer, 45: 904–911, 1982.

Dictionary Of Inorganic Compounds, vol. I, Ac–$C_{10}$, IC–000667–IC–000671.

Flamigni et al., "Effect of Sodium Arsenite on the Induction and Turnover of Ornithine Decarboxylase Activity in Erythorleukemia Cells", Cell Biochemistry and Function 7:213–217, 1989, Fluka, 1995/96 Catalog:152–153.

Forkner et al., "Arsenic as a therapeutic agent in chronic myelogenous leukemia", Jour. A.M.A. 97(1):3–5, 1931.

Germolec et al., "Arsenic induces over expression of growth factors in human keratinocytes", Toxicology And Applied Pharmacology, 141: 308–318, 1996.

Ishinishi N. et al., "Study on Chronic Toxicity of Arsenic Trioxide in Rats with Special Reference to the Liver Damages", Fukuok Acta Medicine, 71:27, 1980.

Kasper et al., "Hepatic Angiosarcoma and bronchioloalveolar carcinoma induced by Fowler's solution", JAMA 252(24):3407–3408, 1984.

Kerkvliet et al., "Immunotoxicology Studies of Sodium Arsenate–effects of Exposure on Tumor Growth and Cell–mediated Tumor Immunity", J Environmental Pathology and Toxicology, 4:65–79, 1980.

König et al., "Comparative Activity of Melarsoprol and Arsenic Trioxide in Chronic B–Cell Leukemia Lines", Blood 90(2):562–570, 1997.

Kwong et al., "Delicious Poison: Arsenic Trioxide fro the treatment of Leukemia", Blood 89:3487–8, 1997.

Lee et al., "Induction of Gene Amplification by Arsenic", Science, 241: 79–81, 1988.

Li et al., "Traditional Chinese and Western Medicine in the Treatment of 27 Patients with Malignant Lymphoma", Chinese J Oncology, 10:61–62, 1988.

Lu et al., "Effective treatment of AML–M3 (APL) and their remission maintenance with Realgar: A pilot clinical and laboratory study on 38 patients", Blood 90(10 Suppl. 1, part 1):416A, #1849, 1997.

Lu et al., Study of Realgar in the treatment of acute promyelocytic Leukemia (APL)—a pilot clinical and laboratory study on 32 Patients, China–Korea Medical Conference '97, 1997.

Mervis, "Ancient remedy performs new tricks", Science 273: 578, 1996.

Monfardini et al., "Survival in chronic myelogenous leukemia: influence of treatment and extent of disease at diagnosis", Cancer, 31: 492–501, 1973.

Neubauer, "Arsenic Cancer: a review", Arsenical Cancer, Arsenic Committee of the Medical Research Council, pp. 192–251, 1947.

Pershagen et al., "On the pulmonary tumorigenicity of arsenic trisulfide and calcium arsenate in hamsters", Cancer Letters, 27: 99–104, 1985.

Pories et al., "Trace Elements that Act to Inhibit Neoplastic Growth", Annals New York Academy of Sciences, 199:pp 265–273, 1972.

Reichl et al., "Effect of Arsenic on Cellular Metabolism after Single or Repeated Injection in Guinea Pigs", Arch. Toxicol., Suppl. 13, p. 363–65, 1989.

Remington's Pharmaceutical Sciences, Mack Publishing Co., Easton, PA, p. 1570–80, 1990.

Schenk, Handbook of Preparative Inorganic Chemistry, 1: 603, G. Brauer, Ed., Academic press, New York, 2nd Ed., 1963.

Shen et al., "Use of arsenic trioxide ($As_2O_3$) in the treatment of acute promyelocytic Leukemia (APL): II. clinical efficacy and pharmacokinetics in relapsed patients", Blood 89(9):3354–3360, 1997.

Shibuya, "Studies on Experimental Arsenious Acid Poisoning", Tokyo Jikeikai Ika Daigaku Zasshi 86(4):653, 1971.

Soignet et al., "Complete Remission after Treatment of Acute Promyelocytic Leukemia with Arsenic Trioxide", J of Medicine 339:19, 1998.

Stephens et al., "The therapeutic effect of solution of potassium arsenite in chronic myelogenous leukemia", Ann. Intern. Assoc 9:1488–1502, 1936.

Suehiro Shimotsuura et al., "Studies on the Antineoplasmic Actions of $As_2O_3$", Shikwa Gakuho 86: 1237–1253, 1986.

Treleaven et al., "Arsenic and Ayurveda", *Leukemia and Lymphoma* 10:343–345, 1993.

USP Dictionary of USAN and International Drug Names, United states Pharmacopeial Conventions, Inc., Rockville, MD, p. 59, Nov., 1994.

Wang et al., "Studies on chemically preventing leukemia", Chung Hua Chung Liu Tsa Chih, 11(3): 207–210, 1989.

Yamamoto et al., "Tumorigenicity of inorganic arsenic compounds following intratracheal instillations to the lungs of hamster", Int. J. Cancer, 40: 220–223, 1987.

Zhang et. al., "Treatment of Acute Promyelocytic Leukemia with "713": Clinical Observations and Study of Action Mode on 117 patients", J Harbin Medical Univ. 29(3): 243, 1995.

Zhang et al., "Treatment of Acute Promyelocytic Leukemia with Intravenous Arsenic Trioxide", Chinese J. of Hematology 17(2): 1996.

Zhang et al., "Discussion on methods for removing As involving use of yogurt", Zhongguo Zhongyao Zaahi, 20(9): 537, 1995.

Zhu et al., "Arsenic–induced PML targeting onto nuclear bodies: implications for the treatment of acute promyelocytic leukemia", Proc.Natl.Acad. Sci. 94:3978–3983, 1997.

"Letter on Historical Facts Regarding the Development of Ai Ling No. 1 and the Clinical Use of Arsenic Trioxide in the Treatment of Acute Promyelocytic Leukemia and a Study of it Mechanism," Heilongjiang Branch of the Chinese Medical Association, Mar. 27, 1998.

Wang et al., "Arsenic Trioxide and Melarsprol Induced Programmed cell death in myeloid luekemia cell lines and function in PML and PNL–RARα Independent Manner," Blood, 92(5):1497–1504, 1998.

* cited by examiner

COMPOSITIONS AND METHODS FOR THE TREATMENT OF PRIMARY AND METASTATIC NEOPLASTIC DISEASES USING ARSENIC COMPOUNDS

This application claims the benefit of U.S. Provisional Application 60/062,375, filed on Oct. 15, 1997.

FIELD OF INVENTION

The present invention relates to methods and compositions for the treatment of primary and metastatic neoplastic diseases, including, but not limited to human sarcomas, carcinomas and hematopoietic disorders. In the practice of the treatment of cancer, compositions containing arsenic compounds are used to arrest and reverse neoplastic growth.

More specifically, the present invention relates to novel chemotherapeutic methods—novel uses of arsenic compounds for treating primary and metastatic tumors; primary and metastatic tumors of the central nervous system; refractory primary and metastatic tumors of the central nervous system; breast, lung, bladder and prostate cancer; and refractory breast, lung, bladder and prostate cancer to mention a few.

BACKGROUND OF THE INVENTION

In 1997 more than one million people will develop some type of cancer in the United States. Approximately 500,000 will be cured or in a state of remission. These numbers represent an improving cure rate seen over the past decade which is largely due to earlier detection, better treatment and advances in chemotherapy. In particular, the advances in chemotherapy include targeted or specific drug therapy in which a drug is developed specifically for the treatment of a certain cancer type. This "disease-oriented" approach is designed to identify compounds which exert selective effects in vitro on particular tumor types and to follow-up these leads in vivo utilizing cell lines, (Fiebig et al., *Cancer Treatment Reviews* 17:109–117 (1990)). However, the incidence of cancer is continuing to climb as our population ages and as new cancers develop or occur more frequently, such as in patients infected with AIDS virus. Thus, it is clear that there is a tremendous demand for additional regimens to treat patients with cancer.

Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, *Basic Pathology*, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., 1993, Immunology, 3rd ed., Mosby, St. Louis, pps. 17.1–17.12).

AIDS-related Non-Hodgkin's Lymphoma

Since the discovery of AIDS, the disease has had a close association with an interesting spectrum of cancers. Further, the types of malignancies and their incidence rates are increasing as the development of effective antiretroviral therapies and prophylaxis against opportunistic infections leads to prolonged survival in the immunodeficient state for AIDS patients, (Karp and Broder, *Cancer Res.* 51:4747–4756 (1991)). AIDS-related non-Hodgkin's lymphoma was found to occur in AIDS patients only after 1981. AIDS-related non-Hodgkin's lymphoma is a very aggressive disease with a very high incidence of central nervous system involvement. It is increasing in incidence in the AIDS population. As patients infected with the AIDS virus now live longer because they are not dying of the usual infections, they are developing lymphoma at an increasing rate. The characteristics of AIDS-related non-Hodgkin's lymphoma are detailed in an article by Karp and Broder, (1991), supra.

The problems the medical oncologist has in treating patients with AIDS-related lymphomas is the recently described predilection for occurrence of the lymphoma in the central nervous system (in brain and surrounding meninges) and the fact that the patient with AIDS has a very weak bone marrow which cannot tolerate treatment with standard chemotherapy. This makes the treatment of lymphoma in patients with AIDS very difficult because standard chemotherapeutic agents are usually very marrow suppressive and do not cross blood brain barrier (to treat the central nervous system disease).

Primary and Metastatic CNS Tumors

The incidence of primary and metastatic brain tumors is increasing in the United States. Indeed, the arsenal of chemotherapeutics for these types of cancers is minimal, while the need for such therapeutics is high.

Glioblastoma multiform and other primary and metastatic central nervous system tumors are devastating malignancies. The treatment of these tumors include surgery, radiation therapy and treatment with agents such as the nitrosourea BCNU. Other chemotherapeutic agents utilized include procarbazine, vincristine, hydroxyurea and cisplatin. Unfortunately, even when all three modalities (surgery, radiation therapy and chemotherapy) are utilized, the average survival of patients with central nervous system malignancies is still about 57 weeks. Clearly, new treatment approaches are needed both for patients with newly diagnosed primary and metastatic central nervous system tumors, as well as for patients with such tumors which are refractory to the above modalities. Finding such new agents has been complicated by the fact that there is no animal model which appears to predict what agent will be clinically effective against primary and metastatic central nervous system tumors.

Breast, Lung, Bladder and Prostate Cancers

Breast cancer has been known to occur in about one in every 8–9 women in the United States. The treatment for early breast cancer is surgery, with or without radiation therapy, or surgery, with or without radiation therapy, plus chemotherapy and/or hormonal therapy. Despite the best efforts of physicians there are still more than 80,000 deaths each year from breast cancer and the incidence is still rising. Current chemotherapy for patients with primary or metastatic breast cancer includes treatment with cyclophosphamide, methotrexate, doxorubicin, 5-fluorouracil, cisplatin, vinblastine, taxol, taxotere, mitomycin C and occasionally other agents. Unfortunately, even with these agents, almost all women who develop metastatic breast cancer succumb to their disease. One particular place that metastatic breast cancer does metastasize to is the central nervous system. When central nervous system metastases do occur, the usual treatment is surgery (for a solitary metastasis) or radiation, or surgery plus radiation therapy. At present there is no chemotherapy which is felt to be helpful in this situation.

Lung cancer is responsible for more than 150,000 deaths each year in the United States. Most patients with lung cancer present a tumor that has already metastasized to a variety of organs, including lung, liver, adrenal gland and other organs. The current treatment for metastatic lung cancer is not yet standardized (Ihde, Daniel C., "Chemotherapy of Lung Cancer", *The New England Journal of Medicine* 327:1434–1441, 1992 Nov. 12th issue). However, chemotherapy regimens which are utilized include treatment with cisplatin plus etoposide, combinations of cyclophosphamide plus doxorubicin plus cisplatin, and single agents alone or in combination, including ifosfamide, teniposide, vindesine, carboplatin, vincristine, taxol, nitrogen mustard, methotrexate, hexamethylmelamine and others. Despite these chemotherapeutic regimens the average patient with metastatic lung cancer still only survives 7–12 months. One particular troublesome place for metastases of lung cancer is the central nervous system. The treatment for central nervous system metastases includes surgery (to remove a solitary lesion), radiation therapy, or a combination of both. Unfortunately, there is not standard chemotherapy which is felt to be helpful in this situation.

Each year about 11,000 patients die of bladder cancer in the U.S. Although at presentation the disease is usually localized, most patients develop distant metastatic disease. The most recent advances have been in the area of chemotherapy for patients with such metastatic disease. One effective regimen is called the MVAC regimen. It consists of treatment with methotrexate plus vinblastine plus adriamycin (doxorubicin) plus cisplatin. Although the response rate is high to this chemotherapeutic regimen, medical oncologists are noting that one place the patients fail is with metastases to the central nervous system. Unfortunately, there is no standard chemotherapy which is felt to be helpful in this situation.

It is estimated that more than 100,000 men will be diagnosed with prostate cancer this year and more than 30,000 patients will die from the disease. The most common sites of metastases in patients with prostate cancer are the bone and lymph nodes. The bone metastases are particularly bothersome in that they can create intense pain for the patient. The current treatment for metastatic prostate cancer includes treatment with flutamide, leuprolide, diethylstilbestrol, and other hormonal manipulations, as well as chemotherapy (doxorubicin, estramustine phosphate, vinblastine, suramin, cisplatin, and others). Unfortunately, none of these agents are consistently helpful in the disease. In addition, as patients with prostate cancer live longer with their malignancy, they will most likely develop a higher incidence of metastases to the central nervous system (including the spinal cord).

In general, as patients are living longer with the common malignancies such as breast cancer, lung cancer, bladder cancer, prostate cancer and a variety of other malignancies (because of control of their systemic disease with surgery, radiation therapy and chemotherapy), oncologists are noting that they are developing an increasing incidence of metastatic tumors in the central nervous system including the brain. This is probably because most of the currently available chemotherapy does not cross the blood brain barrier. When the patient (who has their tumor controlled in sites outside of the brain) develops brain metastases, it is a very difficult situation. Options for that patient are usually limited to surgery for a solitary metastasis and/or radiation therapy. However, after those modalities fail, the patient usually has no other options.

For each of the above indications (primary brain tumors and metastases to the brain from other common tumors such as breast, lung, bladder and prostate cancers), there is a tremendous need for a more effective treatment and/or methods for improving the quality of patient life.

Esophageal Cancer

In the U.S., carcinoma of the esophagus represents about 6% of all cancers of the gastrointestinal tract but causes a disproportionate number of cancer deaths. (Boring, C. C., et al.: Cancer statistics, 1993. *CA Cancer J. Clin.* 43:7, 1993). These cancers usually arise from the epithelial layer of the esophagus and are either squamous cell carcinomas or adenocarcinomas. Overall the 5 year survival is about 5%.

Squamous cell carcinoma generally occurs after the age of 50 and is more common in males than in females. The incidence varies widely from country to country and between regions within countries. In the U.S. the incidence is between 2 and 8 persons per 100,000 and is more prevalent in blacks than in whites.

Adenocarcinoma represents 25% of all esophageal CA in the U.S. It is usually located in the distal one third of the esophagus and may invade the adjacent gastric cardia. It tends to occur in people over 40 years of age and is more common in males than in females. It is more common in whites than in blacks.

Arsenic And Its Medical Uses

Arsenic has been considered to be both a poison and a drug for a long time in both Western and Chinese medical practices. In the latter part of the nineteenth century, arsenic was used frequently in attempts to treat diseases of the blood in the West. In 1878, it was reported that treatment of a leukemic patient with Fowler's solution (a solution of potassium arsenite) reduced markedly the count of white blood cells (Cutler and Bradford, *Am. J. Med. Sci.*, January 1878, 81–84). Further interests in the use of Fowler's solution as a palliative agent to treat chronic myelogenous leukemia (CML) was described by Forkner and Scott in 1931 (*J. Am. Med. Assoc.*, 1931, iii, 97), and later confirmed by Stephens and Lawrence in 1936 (*Ann. Intern. Med.* 9, 1488–1502). Typically, Fowler's solution was orally administered to leukemic patients as a solution until the level of white blood cells was depressed to an acceptable level or until toxicities (such as skin keratoses and hyperpigmentation) developed, while the patients enjoyed varying periods of remission. In the 1960's, Fowler's solution was still used occasionally in attempts to treat CML, however, most patients with CML were treated with other chemotherapeutic agents, such as busulfan, and/or radiation therapy (Monfardini et al., *Cancer*, 1973, 31:492–501).

Paradoxically, one of the long recognized effects of exposure to arsenic, whether the source is environmental or medicinal, is skin cancer (Hutchinson, 1888, *Trans. Path. Soc. Lond.*, 39:352; Neubauer, 1947, *Br. J. Cancer*, 1:192). There were even epidemiological data to suggest that the use of Fowler's solution over long periods could lead to an increased incidence of cancer at internal sites (Cuzick et al., *Br. J. Cancer*, 1982, 45:904–911; Kaspar et al., *J. Am. Med. Assoc.*, 1984, 252:3407–3408). The carcinogenicity of arsenic has since been demonstrated by the fact that it can induce chromosomal aberration, gene amplification, sister chromatid exchanges and cellular transformation (See e.g., Lee et al., 1988, *Science*, 241:79–81; and Germolec et al., *Toxicol. Applied Pharmacol.*, 1996, 141:308–318). Because of the known carcinogenic effect of arsenic, its only therapeutic use in human in Western medicine today is in the treatment of tropical diseases, such as African trypanosomiasis, (melarsoprol, or Arsobal® by Rhône Poulenc Rorer, Collegeville, Pa.; See Goodman & Gilman's The Pharmacological Basis of Therapeutics, 9th edition, chapter 66, 1659–1662, 1997).

In traditional chinese medicine, arsenous acid or arsenic trioxide paste has been used to treat tooth marrow diseases, psoriasis, syphilis and rheumatosis (Chen et al., 1995, in Manual of Clinical Drugs, Shanghai, China, Shanghai Institute of Science and Technology, p.830). In 1970s, arsenic trioxide had been applied experimentally to treat acute promyelocytic leukemia (APL) in China (commented by Mervis, 1996, *Science*, 273:578). The clinical efficacy of arsenic trioxide has recently been re-investigated in 14 of 15 patients with refractory APL, where the use of an intravenous dose at 10 mg/day for 4–9 weeks was reported to result in complete morphologic remission without associated bone marrow suppression (Shen et al., 1997, *Blood*, 89:3354–3360). It was also reported that arsenic trioxide induced apoptosis (programmed cell death) in vitro in NB4 cells, an APL cell line, and that apoptosis was apparently associated with down-regulation of the oncogene bcl–2, and intracellular redistribution of the chimeric PML/RARα protein that are unique to APL cells (Chen et al., 1996, *Blood*, 88:1052–1061; Andre et al., 1996, *Exp. Cell Res.* 229:253–260). Similarly, melarsoprol has been reported to induce apoptosis in cell lines representative of chronic B-cell leukemia (Konig et al., 1997, *Blood* 90:562–570). Whether apoptosis is induced in APL patients is presently unclear, but it is believed by some to be one of the possible mechanisms of the therapeutic effects of certain arsenic compounds.

Although arsenic is well known to be both a poison and a carcinogenic agent, there have been many reports concerning the use of arsenic in medical treatment. Identification or discussion of the art above must not be construed as an admission that such is prior art.

Further, from the above discussion, it should be clear that there are a plethora of different types of cancers, each of which requires a unique treatment protocol. Thus, the development of a broad spectrum anti-cancer agent is extremely desirable. At a minimum, additional effective anti-cancer agents are needed to be added to the arsenal against cancer.

SUMMARY OF THE INVENTION

Notwithstanding the conflicting reports in the art concerning benefits and risks of the administration of arsenic to patients, applicants have discovered that arsenic compound has broad applicability in the treatment of various cancers, including solid tumors and blood disorders. For example, the present invention encompasses the use of arsenic in the form of a salt, complex, organic compound or ionic solution to treat tumors of epithelial tissue, connective tissue, central nervous system, lymphoid tissue, hematopoietic cells and tumors associated with oncogenic viruses.

Further, the present invention encompasses the use of arsenic compounds to treat mammals suffering from primary and metastatic neoplastic disease as well as infectious diseases related thereto.

In addition, this invention also encompasses the use of arsenic compounds to treat primary and metastatic breast lung, bladder and prostate cancers in humans.

This invention also encompasses the treatment of hematopoietic disorders in mammals by the administration of one or more arsenic compounds to said mammal. The hematopoietic disorders to be treated include but are not limited to polycythemia vera, Hodgkin's Disease, non-Hodgkin's Disease including Follicular Lymphoma, Diffuse Lymphoma, lymphoblastic lymphoma, small lymphocytic lymphoma, acute lymphocytic leukemia, hairy cell leukemia, myeloid metaplasia, myeloid dysplastic syndrome, multiple myeloma and plasmacytoma.

In accordance with the present invention, arsenic compounds can be used alone or in combination with other known therapeutic agents (including chemotherapeutics, radioprotectants and radiotherapeutics) or techniques to either improve the quality of life of the patient, or to treat the primary neoplastic disease. For example, the arsenic compounds can be used before, during or after the administration of one or more known antitumor agents including but not limited to mustard compounds, nitrogen mustard, chlorambucil, melphalan, cyclophosphamide, 6-mercaptopurine, 6-thioguanine, cytarabine, 5-fluorouracil, floxuridine, methotrexate, vincristine, vinblastine, taxol, etoposide, temiposide, dactinomycin, daunorubicin, doxorubicin, bleomycin, mitomycin, cisplatin, carboplatin, estramustine phosphate, hydroxyurea, BCNU, procarbazine, VM-26 (vumon), interferons and all-trans retinoic acid (ATRA), (See for example, the Physician Desk References 1997). In addition, the arsenic compounds can be used before, during or after irradiation treatment. For the treatment of HIV-infected individuals, the arsenic compounds can be used alone or in combination with AZT, ddI, ddA, ddC, d4T, 3TC and other known antiviral agents.

The invention described herein encompasses a method of treating primary and metastatic neoplastic diseases, a method of treating solid tumors, a method of treating leukemias, a method of treating cancers related to bcl–2 (oncogene), each of which comprises the administration of a therapeutically effective and non-lethal amount of one or more arsenic compounds to a mammal in need of such therapy. The invention, as mentioned above also encompasses the use of combination therapy to treat the aforementioned diseases.

In a particular embodiment, the arsenic compounds are used within a method to treat breast, lung, colon, ovarian, renal, non-small cell lung, central nervous system, bladder, prostate and head and neck cancer by administering an effective amount of one or more arsenic compounds alone or in combination with other antineoplastic agents or therapeutic techniques including radiotherapy and surgery.

Without being limited by any theory, the inventors believe that the arsenic compounds of the invention may have one or more mechanisms of action in connection with the methods described herein. For example, the arsenic compounds may act as a phosphorous analogue which interferes with the phosphorylation events that occur in signal transduction involved in apoptosis. Arsenic may also act as an inhibitor of angiogenesis, i.e., the formation of new blood vessels, thereby limiting blood flow to proliferating preneoplastic cell masses, tumors and metastases. It is well known that if a tumor is not invaded by blood capillaries, it would have to depend on the diffusion of nutrients from its surroundings and cannot enlarge beyond a certain size. Arsenic may also function as a differentiating agent which causes dividing preneoplastic and/or cancer cells that display an undifferentiated or underdifferentiated phenotype to develop into terminally differentiated cells, and die after a finite number of cell divisions. Finally, arsenic may also act to sensitize the cancer cells to radiation and/or chemotherapy. Thus, the arsenic compounds of the invention are described as being useful against a variety of cancers.

Specific therapeutic regimens, pharmaceutical compositions, and kits are also provided by the invention. Thus, the invention also encompasses pharmaceutical compositions which comprise one or more arsenic compounds and a pharmaceutically acceptable carrier. The compositions are sterile solutions suitable for intravenous injection or infusion. In another embodiment the invention encompasses a composition suitable for oral delivery; comprising one or more arsenic compounds and a pharmaceutically acceptable excipient or carrier. In another embodiment, the invention also includes compositions suitable for topical or dermal delivery.

Particular compositions of the invention and their properties are described in the sections and subsections which follow.

BRIEF DESCRIPTION OF THE DRAWINGS

FIG. 1A. Leukemic cell lines CCRF-CEM, HL-60 (TB), K-562, MOLT-4, RPMI-8226, SR. FIG. 1B. Non-Small Cell Lung Cancer cell lines A549/ATCC, EKVX, HOP-62, HOP-92, NCI-H226, NCI-H23, NCI-8322M, NCI-H460, NCI-H522. FIG. 1C. Colon Cancer cell lines COLO 205, HCT-116, HCT-15, HT29, KM12, SW620. FIG. 1D. CNS Cancer cell lines SF-268, SF-295, SF-539, SNB-19, SNB-75, U251. FIG. 1E. Melanoma cell lines LOX 1MV1, MALME-3M, M14, SK-MEL-2, SK-MEL-28, SK-MEL-5, UACC-257, UACC-62. FIG. 1F. Ovarian Cancer cell lines IGROV1, OVCAR-3, OVCAR-5, OVCAR-8, SK-OV-3. FIG. 1G. Renal Cancer cell lines A498, CAKI-1, RXE 393, SN12C, TX-10, UO-31. FIG. 1H. Prostate Cancer cell lines PC-3, DU-145. FIG. 1I. Breast Cancer cell lines MCF7, NCI/ADR-RES, MDA-MB-435, MDA-N, BT-549, T-47D.

FIG. 3A. Leukemic cell lines CCRF-CEM, K-562, MOLT-4, RPMI-8226. FIG. 3B. Non-small Cell Lung Cancer cell lines EKVX, HOP-62, HOP-92, NCI-H226, NCI-H23, NCI-H322M, NCI-H460, NCI-H522. FIG. 3C. Colon Cancer cell lines COLO 205, HCT-116, HCT-15, HT29, KM12, SW-620. FIG. 3D. CNS Cancer cell lines SF-268, SF-295, SF-539, SNB-75, U251. FIG. 3E. Melanoma cell lines LOX IMVI, MALMI-3M, SK-MEL-2, SK-MEL-28, SK-MEL-5, UACC-257, UACC-62. FIG. 3F. Ovarian Cancer cell lines IGROVI, OVCAR-3, OVCAR-5, OVCAR-8, SK-OV-3. FIG. 3G. Renal Cancer cell lines 786-O, A498, CAKI-1, RXF 393, S12C, TK-10. FIG. 3H. Prostate Cancer cell lines DU-145. FIG. 3I. Breast Cancer cell lines MCF7, NCI/ADR-RIS, MDA-MB-231/ATCC, HS 578T, MDA-MB-435, MDA-N, BR-549, T-47D.

DETAILED DESCRIPTION OF THE INVENTION

Figure 1A:
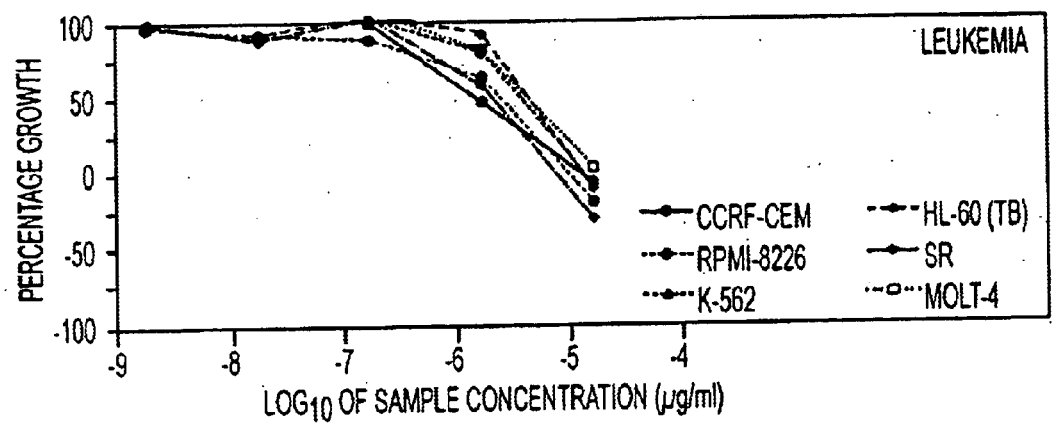
FIGS. 1A–1I. Dose response curves showing percentage growth of various cancer cell lines after continuous exposure to $10^{-5}$ to $10^{-9}$ μ/ml of arsenic trioxide for 2 days.
Figure 1B:
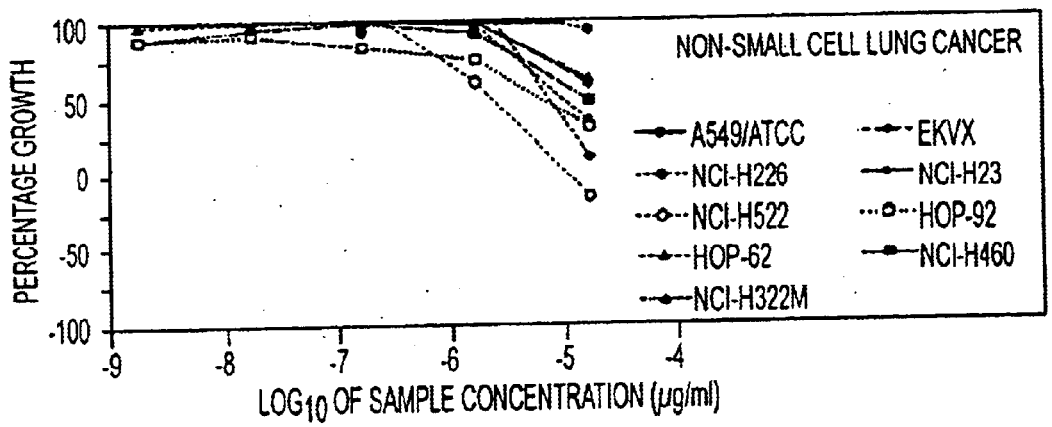
Figure 1C:
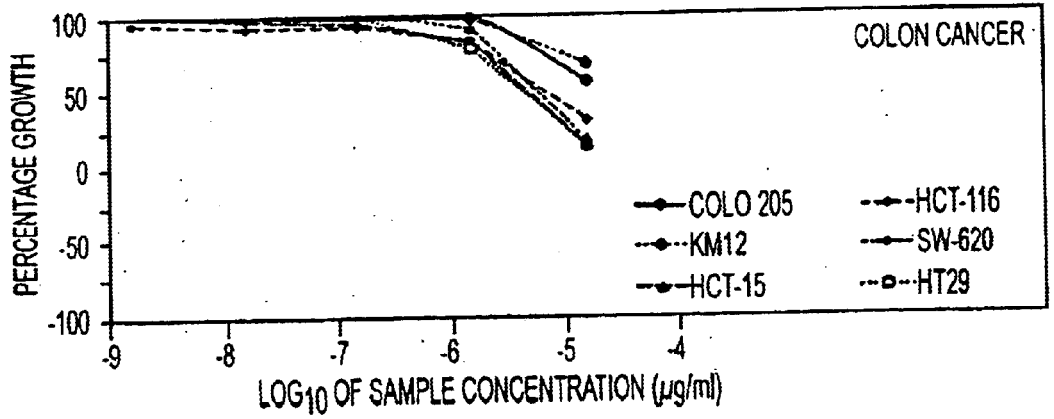
Figure 1D:
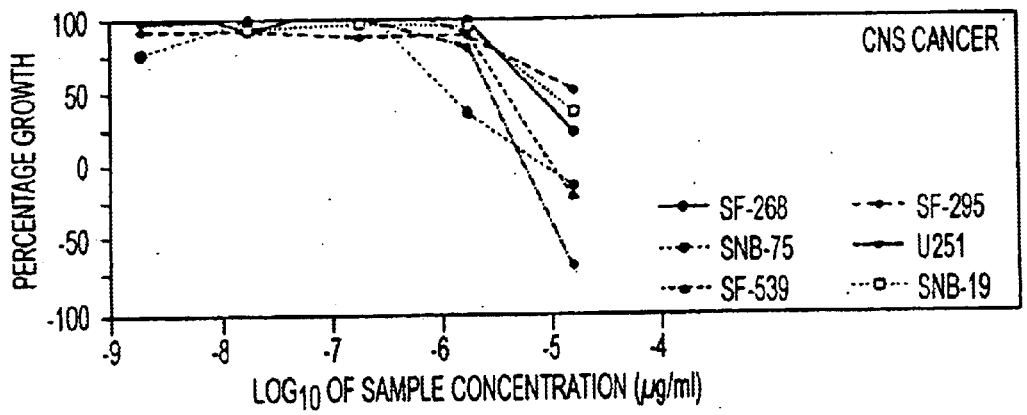
Figure 1E:
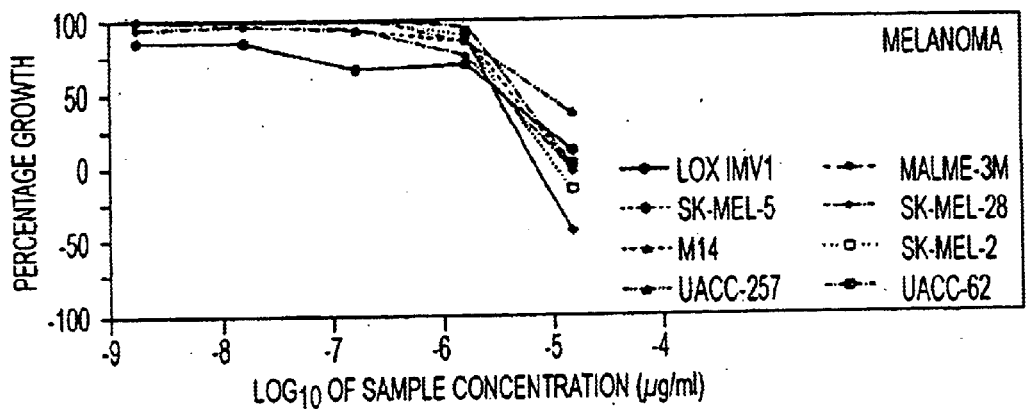
Figure 1F:
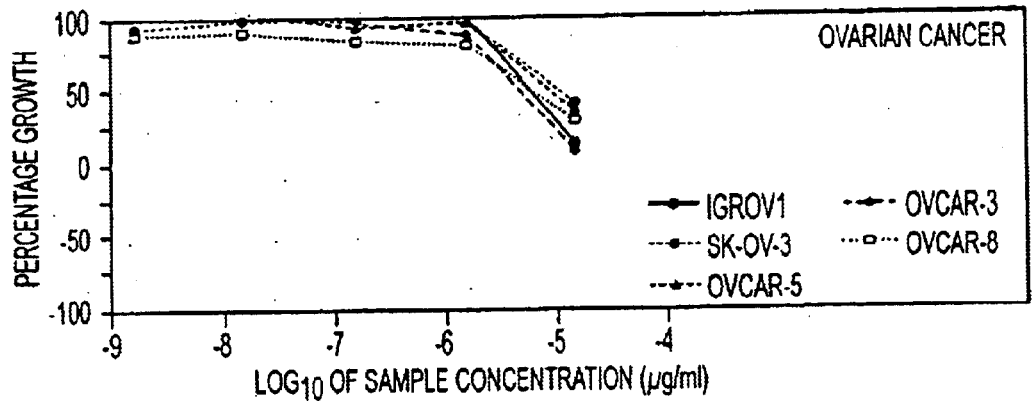
Figure 1G:
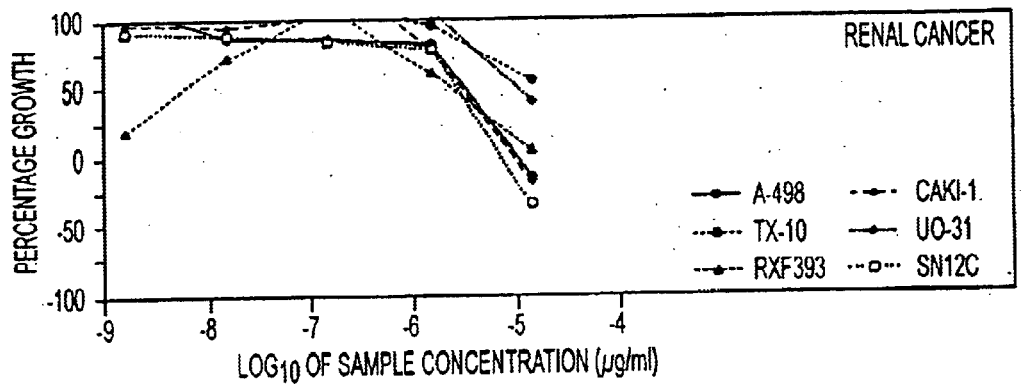
Figure 1H:
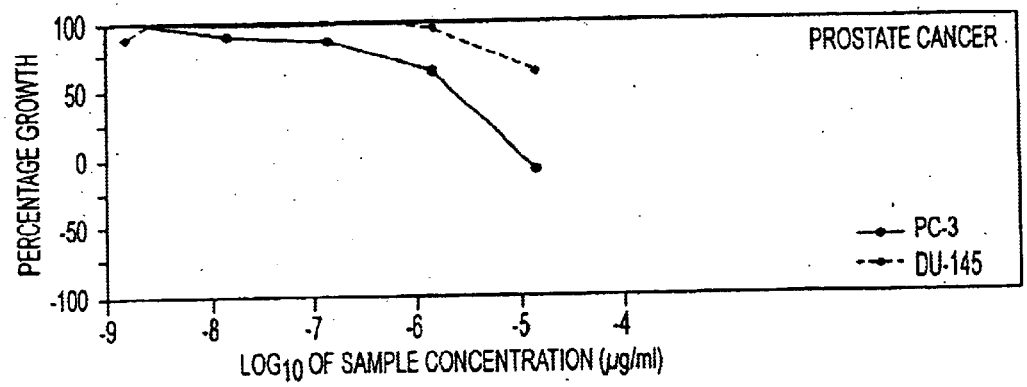
Figure 1I:
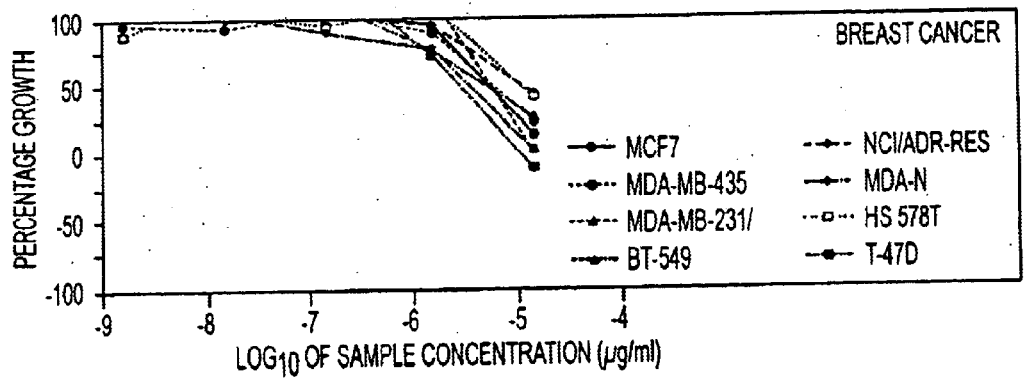

Methods and compositions for the treatment of primary and metastatic neoplastic diseases are described herein. The invention is based, in part, on a dosage regimen for administration of compositions comprising arsenic. The invention is also based in part, on the potency of the arsenic compounds of the invention against certain cancers.

This invention includes a method of treating primary solid tumors in a mammal which comprises administering to a mammal in need of such therapy a therapeutically effective and non-lethal amount of one or more arsenic compound.

The invention also includes a method of treating metastatic tumors in a mammal which comprises administering to a mammal a therapeutically effective and non-lethal dose of one or more arsenic compound.

The invention includes a method for treating disorders of blood in mammal which comprises administering one or more arsenic compound in a therapeutically effective and non-lethal amount.

The arsenic compound of the invention may be utilized in in a variety of known forms; for example, arsenic can be administered as a salt, an organic or inorganic complex, an organic chelate, an organic compound or an organic or inorganic solution. It is preferred that the form be chosen to reduce toxicity and improve efficacy. Further, the form chosen may also depend on the type and location of the tumor in question. The inorganic salt forms of arsenic are preferred. For example, inorganic salts such as arsenic triiodide, arsenic(III)bromide, arsenic(III)chloride, arsenic pentoxide, arsenic trioxide, Fowler's solution (potassium arsenite), sodium arsenite, and calcium arsenite may be used. Arsenic trioxide is most preferred. Both arsenous acids and arsenites as well as arsenic acids and arsenates may be used within the present methods. Aqueous solutions containing arsenite ions are preferred. Further, arsenic sulfides may be used such as arsenous sulfide, arsenic sulfide, arsenic pentasulfide, tetraarsenic trisulfide and tetraarsenic pentasulfide. Without being limited by any theory, certain of these arsenic compounds may be prodrugs to an active species.

Generally, the skilled artisan will recognize that the form of arsenic to be used should be therapeutically effective without unreasonable toxicity. The toxicity is dependent upon the dose, the dosage form, the mode of administration and frequency of dosing. Generally, the skilled artisan can chose from the following known forms of arsenic: arsenic halides, arsenic oxides, arsenic acids, arsenic sulfides, and the like.

Arsenic can also be readily combined with carbon to form a wide variety of organic compounds. These include but are not limited to primary and secondary arsines, tertiary arsines, halo arsines, dihalo arsines, cyclic and polymeric substances containing arsenic; specific examples of organic arsenic compounds include but are not limited to 3-Nitro-4-hydroxyphenylarsonic acid, arsanilic acid, sodium hydrogen 4-aminophenylarsenate, melarsoprol, melarsonyl potassium, carbarsone, arsenamide arsphenamine and sodium arsanilate.

As used herein, "arsenic compound" refers to a pharmaceutically acceptable form of arsenic including salts, solutions, complexes, chelates and organic and inorganic compounds incorporating arsenic. It should be recognized that the invention includes arsenic prodrugs or compounds that are converted in vivo to biologically active forms of arsenic. Such prodrugs may be used to reduce or avoid the well known potential for arsenic toxicity. The arsenic compounds of the present invention can be synthesized or commercially purchased. For example, the compounds can be prepared from well-known chemical techniques. (See for example, Kirk-Othmer, Encyclopedia of Chemical Technology 4 ed. volume 3 pps. 633–655 John Wiley & Sons).

In one embodiment, the arsenic compound of the invention is arsenic trioxide which is dissolved in an aqueous solution of sodium hydroxide, with the pH adjusted to a physiologically acceptable range, e.g. about pH 6–8.

Any suitable mode of administration may be used in accordance with the present invention including but not limited to parenteral administration such as intravenous, subcutaneous, intramuscular and intrathecal administration; oral, intranasal, rectal or vaginal administration may also be used; directly into the tumor; transdermal patches; implant devices (particularly for slow release); finally, topical administration may be used. The mode of administration will vary according to the type of arsenic compound being used and the disease to be treated.

The pharmaceutical compositions to be used may be in the form of sterile physiologically acceptable (aqueous or organic) solutions, colloidal suspensions, creams, ointments, pastes, capsules, caplets, tablets and cachets. The pharmaceutical compositions comprising arsenic compounds of the invention can be contained in sealed sterile glass containers and/or ampoules. Further, the active ingredient may be micro-encapsulated, encapsulated in a liposome, noisome or lipofoam alone or in conjunction with targeting antibodies. It should be recognized that delayed slow or sustained release forms of administration are also included.

The arsenic compounds of the present invention may be used against a variety of primary and metastatic neoplastic diseases including but not limited to primary and metastatic tumors of the central nervous system, breast, colon, ovaries, kidneys, lung, bladder, prostate and head and neck.

More specifically, the arsenic compounds of the present invention can be used to treat tumors of epithelial origin including but not limited to:

squamous cell carcinoma
basal cell carcinoma
melanoma tumors of epithelial lining of glands or ducts:

adenocarcinoma
papillary carcinoma
papillary adenocarcinoma tumors of the liver and biliary tract:

Hepatocellular carcinoma tumors of the gastrointestinal tract:

squamous cell carcinoma of the esophagus
adenocarcinoma of the esophagus
colorectal carcinoma (colon cancer)
gastric carcinoma (stomach cancer)

tumors of respiratory tract:

bronchogenic carcinoma
small cell carcinoma
large cell carcinoma tumors of the urogenital tract:

transitional cell carcinomas of bladder
squamous cell carcinoma of bladder
carcinoma of prostate
carcinoma of cervix tumors of breast tumors of blood cells and related cells (leukemias):

acute and chronic lymphocytic leukemia
polycythemia vera

Cancers of Lymphoid tissue

Malignant Lymphomas - Hodgkins Lymphoma
Non-Hodgkin's Lymphoma- Follicular lymphoma
    Diffuse lymphoma
    Small lymphocytic lymphoma
Large cell lymphoma
Lymphoblastic lymphoma
Multiple myeloma Tumors of Connective Tissue
Cancers of Bone Osteosarcoma Tumors of the Nervous System Neuroblastoma
Retinoblastoma
Glioblastoma
Oligodendroglioma Tumors associated with oncogenic viruses Human Papillomavirus - squamous cell carcinoma of cervix
Ebstein-Barr Virus - Burkitts Lymphoma
    B cell lymphoma's in
    immuno-comprised individuals
    Nasopharyngeal carcinoma
Hepatitis B Virus - Hepatocellular carcinoma Herpes Virus 8 or Kaposi Sarcoma Herpes Virus (KSHV)—Kaposi's Sarcoma, and the like. Other neoplastic diseases known to the skilled artisan are also encompassed by the present invention including cancer of the oral cavity, larynx, kidney, testis and ovary. The skilled artisan will recognize that other cancers may be treated in accordance with the present invention.

The term "a method for treating primary and metastatic tumors of the central nervous system" as used herein means that the disease and the symptoms associated with the disease are alleviated, reduced, cured, or otherwise placed in a state of remission.

As used herein, the terms "a method for treating primary or metastatic breast, lung, bladder or prostate cancer" and "a method for treating metastases from breast, lung, bladder or prostate cancer" means that the disease and the symptoms associated with the disease are alleviated, reduced, cured, or placed in a state of remission. In addition, the term "a method for treating metastases from breast, lung, bladder or prostate cancer" means that the metastatic tumors and the symptoms associated with the disease are alleviated, reduced, cured, placed in a state of remission.

The term "refractory" when used herein means that malignancies are generally resistant to treatment or cure. The term "refractory" when used in the above terms, means that the malignancies which are generally resistant to treatment or cure are alleviated, reduced, cured, or placed in a state of remission.

As used herein the terms "a therapeutic agent", "therapeutic regimen", "radioprotectant", "chemotherapeutic" mean conventional drugs and drug therapies, including vaccines, for treating cancer, viral infections, and other malignancies, which are known to those skilled in the art. "Radiotherapeutic" agents are well known in the art.

As used herein, "a method of treating cancer" or "a method of treating solid tumors" or "a method of treating neoplastic diseases" means that the disease and the symptoms associated with the disease are alleviated, reduced, cured, or placed in a state of remission. Further, tumor growth is inhibited and/or tumor size is reduced.

As used herein, "preneoplastic" cell refers to a cell which is in transition from a normal to a neoplastic form; and morphological evidence, increasingly supported by molecular biologic studies, indicates that preneoplasia progresses through multiple steps. Non-neoplastic cell growth commonly consists of hyperplasia, metaplasia, or most particularly, dysplasia (for review of such abnormal growth conditions (See Robbins and Angell, 1976, Basic Pathology, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. Although preneoplastic lesions may progress to neoplasia, they may also remain stable for long periods and may even regress, particularly if the inciting agent is removed or if the lesion succumbs to an immunological attack by its host.

The therapeutic regimens and pharmaceutical compositions of the invention may be used with additional immune response enhancers or biological response modifiers including, but not limited to, the cytokines IFN-α, IFN-γ, IL-2, IL-4, IL-6, TNF, or other immunostimulatants/immunomodulators. In accordance with this aspect of the invention, the arsenic compounds are administered in combination therapy with one or more of these agents.

Formulation

The arsenic compounds of the invention may be formulated into pharmaceutical preparations for administration to mammals for treatment of cancer. Compositions comprising a compound of the invention formulated in a compatible pharmaceutical carrier may be prepared, packaged, labelled for treatment of and used for the treatment of the indicated tumor, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia (myeloblastic, promyelocytic, myelomonocytic, monocytic and erythroleukemia); chronic leukemia and chronic lymphocytic leukemia; and polycythemia vera, lymphoma (Hodgkin's disease and non-Hodgkin's disease), multiple myeloma, Waldenström's macroglobulinemia, and heavy chain disease. Alternatively, it can be labeled for treatment of the appropriate infectious disease. Alternatively, pharmaceutical compositions may be formulated for treatment of appropriate infectious diseases.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, polyethylene glycol or glycerine. Thus, the compounds and their physiologically acceptable solvates may be formulated for administration by inhalation or insufflation (either through the mouth or the nose) or oral, buccal, parenteral, topical, dermal, vaginal, drug delivery device, e.g., porous or viscous material such as lipofoam, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Such formulations are sterile. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically effective amounts of the arsenic compounds in pharmaceutically acceptable form. The arsenic compound in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of arsenic compounds by a clinician or by the patient.

The magnitude of a therapeutic dose cf an arsenic compound in the acute or chronic management of cancer will vary with the severity of the condition to be treated and the route of administration. The dose, and perhaps dose frequency, will also vary according to the age, body weight, condition and response of the individual patient. In general, the total daily dose ranges for the conditions described herein are generally from about 10 $\mu$g to about 200 mg administered in divided doses administered parenterally or orally or topically. A preferred total daily dose is from about 0.5 mg to about 70 mg of the active ingredient.

Desirable blood levels may be maintained by a continuous infusion of an arsenic compound as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

Again, any suitable route of administration may be employed for providing the patient with an effective dosage of an arsenic compound. For example, oral, rectal, vaginal, transdermal, parenteral (subcutaneous, intramuscular, intrathecal and the like) may be employed. Dosage forms include tablets, troches, cachet, dispersions, suspensions, solutions, capsules, patches, and the like. (See, Remington's Pharmaceutical Sciences.)

The pharmaceutical compositions of the present invention comprise an arsenic compound as the active ingredient, or a pharmaceutically acceptable salt thereof, and may also contain a pharmaceutically acceptable carrier, and optionally, other therapeutic ingredients, for example antivirals. The term "pharmaceutically acceptable salts" refers to salts prepared from pharmaceutically acceptable non-toxic acids and bases, including inorganic and organic acids and bases.

The pharmaceutical compositions include compositions suitable for oral, rectal, mucosal routes, transdermal, parenteral (including subcutaneous, intramuscular, intrathecal and intravenous), although the most suitable route in any given case will depend on the nature and severity of the condition being treated.

In the case where an intravenous injection or infusion composition is employed, a suitable dosage range for use is, e.g., from about 0.5 mg to about 150 mg total daily dose.

In addition, the arsenic carrier could be delivered via charged and uncharged matrices used as drug delivery devices such as cellulose acetate membranes, also through targeted delivery systems such as fusogenic liposomes attached to antibodies or specific antigens.

In practical use, an arsenic compound can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% w/v, normal saline or other solutions. The total dose of the arsenic compound may be administered in a vial of intravenous fluid, e.g, ranging from about 2 ml to about 2000 ml. The volume of dilution fluid will vary according the total dose administered.

Target Cancers

Cancers that can be treated by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia (myeloblastic, myelomonocytic, monocytic and erythroleukemia); and chronic lymphocytic leukemia; and polycythemia vera, lymphoma (Hodgkin's disease and non-Hodgkin's disease), multiple myeloma, Waldenström's macroglobulinemia, and heavy chain disease. Specific examples of such cancers are described in the sections below.

In a specific embodiment the cancer is metastatic. In another specific embodiment, the patient having a cancer is immunosuppressed by reason of having undergone anticancer therapy (e.g., chemotherapy radiation) prior to administration of the arsenic compounds of the invention.

In a specific embodiment, the present invention provides compositions and methods for enhancing tumor specific immunity in individuals suffering from colorectal cancer metastasized to the liver, in order to inhibit the progression of the neoplastic disease. Preferred methods of treating these neoplastic diseases comprise administering a composition of arsenic which elicits an immune response against tumor cells.

In another specific embodiment, the present invention provides compositions and methods for enhancing specific immunity in individuals suffering from hepatocellular carcinoma in order to inhibit the progression of the neoplastic disease and ultimately irradiate all preneoplastic and neoplastic cells.

In a specific embodiment, the present invention provides hsp compositions and methods for enhancing specific immunity to preneoplastic and neoplastic mammary cells in women. The present invention also provides compositions and methods for inhibiting cancer cell proliferation and metastasis. These compositions can be applied alone or in combination with each other or with biological response modifiers.

WORKING EXAMPLES

The following subsections describe the testing of a pharmaceutical composition comprising arsenic trioxide in vitro using a panel of cancer cell lines employed by the National Cancer Institute (NCI). The results demonstrate that arsenic trioxide is effective in inhibiting the growth of a broad range of leukemic cells and cancer cells in vitro.

Methods and Materials

Arsenic trioxide (1 mg/ml, 10 mg/ampoule, manufactured by Taylor Pharmaceuticals, Decatur, Ill.) was tested at five concentrations each at 10-fold dilutions, i.e., $10^{-5}$, $10^{-6}$, $10^{-7}$, $10^{-8}$ and $10^{-9}$ µg/ml.

The in vitro tests were performed by incubating the test cells in the presence of the indicated concentration of arsenic trioxide under standard culture conditions for a designated period of time, which is followed by a sulforhodamine B (SRB) protein assay to estimate cell viability or growth. The cell lines are organized into subpanels according to the origin of the cell lines, e.g., leukemia, breast cancer, etc. A description of the cell lines and method of testing is described in Monk et al. (1997, *Anticancer Drug Des.* 12:533–41) and Weinstein et al., (1997, *Science* 275:343–9), which are incorporated herein in their entirety.

Described below are the data analysis procedures and displays.

The measurement of an effect is expressed in Percentage Growth (PG). The measured effect of the compound on a cell line is calculated according to one or the other of the following two expressions:

If (Mean $OD_{test}$–Mean $OD_{zero}$)≧0. then PG=100×(Mean $OD_{test}$–Mean $OD_{zero}$)/(Mean $OD_{ctrl}$–Mean $OD_{zero}$)

If (Mean $OD_{test}$–Mean $OD_{zero}$)<0. then PG=100×(Mean $OD_{test}$–Mean $OD_{zero}$)/(Mean $OD_{zero}$ where:

Mean $OD_{zero}$=the average of optical density measurements of SRB-derived color just before exposure of cells to the test compounds;

Mean $OD_{test}$=the average of optical density measurements of SRB-derived color after exposure of cells to the test compound for a designated period of time; and Mean $OD_{ctrl}$=the average of optical density measurements of SRB-derived color after with no exposure of cells to the test compound for a designated period of time Table 1 and 2 present the experimental data collected against each cell line. The first two columns describe the subpanel (e.g., leukemia) and cell line (e.g., CCRF-CEM) involved. The next two columns list the Mean $OD_{zero}$ and Mean $OD_{ctrl}$; the next five columns list the Mean $OD_{test}$ for each of five different concentrations. Each concentration is expressed as the $\log_{10}$ (molar or µg/ml). The next five columns list the calculated PGs for each concentration. The response parameters GI50, TGI and LC50 are interpolated values representing the concentrations at which the PG is +50, 0, and −50, respectively. Sometimes these response parameters cannot be obtained by interpolation. If, for instance, all of the PGs in a given row exceed +50, then none of the three parameters can be obtained by interpolation. In such a case, the value given for each response parameter is the highest concentration tested and is preceded by a ">" sign. This practice is extended similarly to the other possible situations where a response parameter cannot be obtained by interpolation.

A dose-response curve (see FIGS. 1A–1I and 3A–3I) for the set of data is created by plotting the PGs against the $\log_{10}$ of the corresponding concentration for every cell line. The cell line curves are grouped by subpanel. Horizontal lines are provided at the PG value of +50, 0, and −50. The concentrations corresponding to points where the curves cross these lines are the GI50, TGI, and LC50, respectively.

Figure 4A:
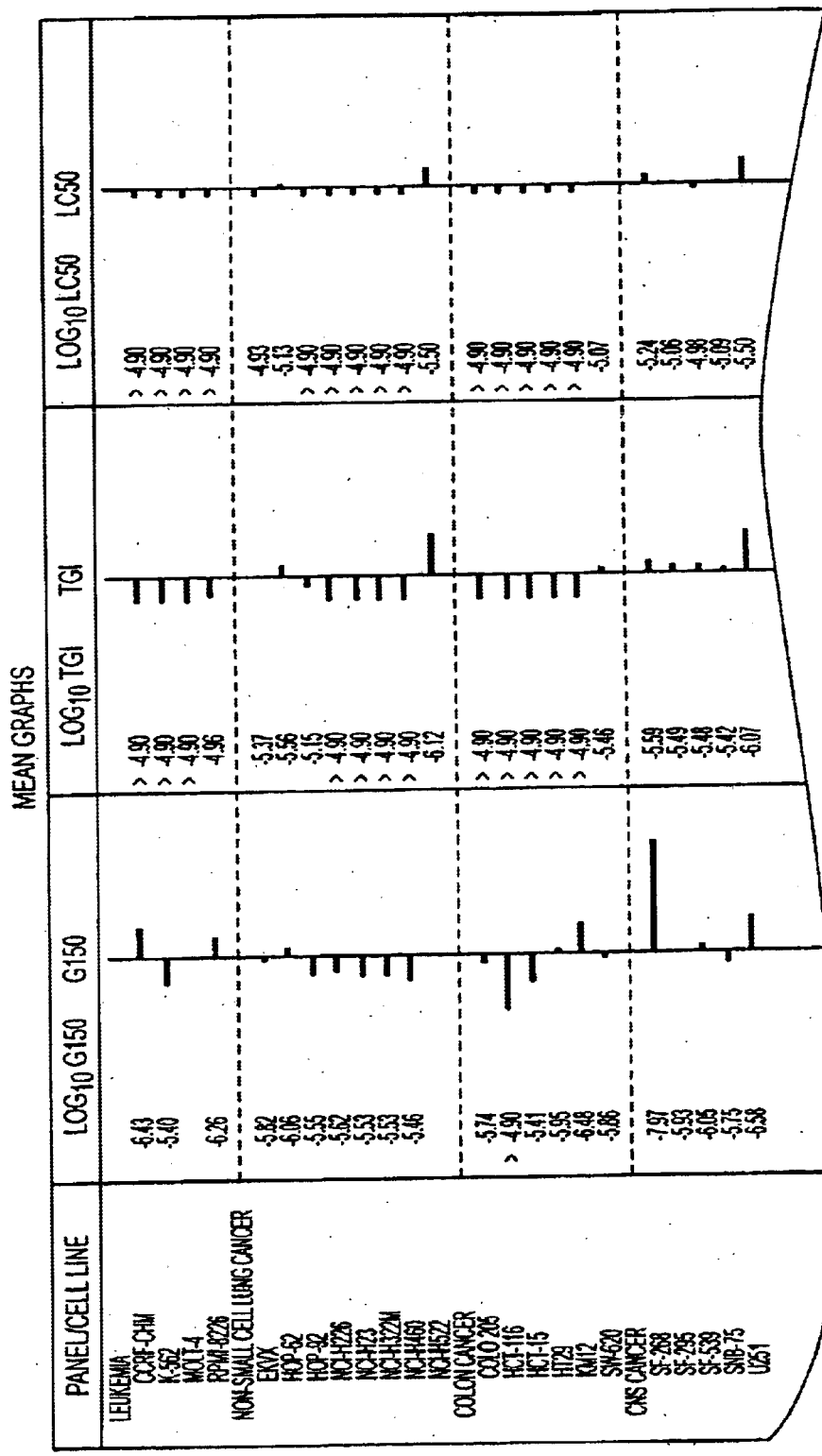
FIG. 4. Mean graphs showing selectivity patterns at each of the principal response parameters for all the cell lines tested after continous exposure to $10^{-5}$ to $10^{-9}$ μg/ml of arsenic trioxide for 6 days.
Figure 4B:
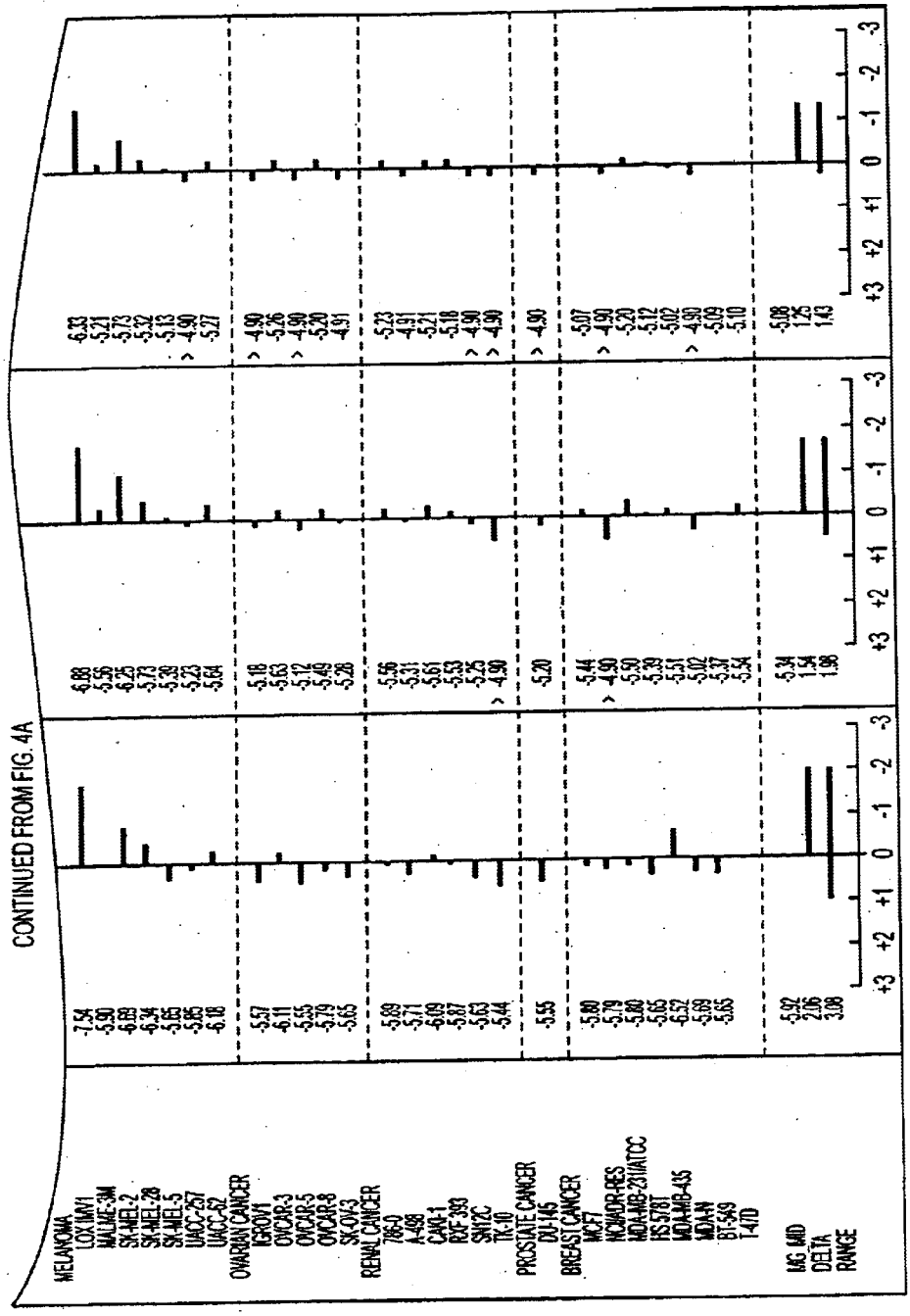

A mean graph (FIGS. 2 and 4) facilitates visual scanning of data for potential patterns of selectively for particular cell lines or for particular subpanels with respect to a selected response parameter. Differences in apparent selectivity patterns may occur for the same compound against the same cell lines when different parameters are compared. The mean graphs page of the data package shows mean graphs at each of the principal response parameters: GI50, TGI, and LC50. Bars extending to the right represent sensitivity of the cell line to the test agent in excess of the average sensitivity of all tested cell lines. Since the bar scale is logarithmic, a bar 2 units to the right implies the compound achieved the response parameter (e.g., GI50) for the cell line at a concentration one-hundredth the mean concentration required over all cell lines, and thus the cell line is unusually sensitive to that compound. Bars extending to the left correspondingly imply sensitivity less than the mean. If for a particular drug and cell line, it was not possible to determine the desired response parameter by interpolation, the bar length shown is either the highest concentration tested (and the listed $\log_{10}$ of the response parameter will be preceded by a ">") or the lowest concentration tested (and the listed $\log_{10}$ will be preceded by a "<").

The values at either limit (> or <) are also calculated in the mean used for the mean graph. Therefore, the mean used in the mean graph may not be the actual mean of the GI50 for instance. For this reason, this value is referred to as the MG_MID (for mean graph midpoint).

Results

The results of two sets of tests is presented below. In the first set, the cells from 56 different cancer cell lines were exposed to five concentrations of arsenic trioxide continuously for two days prior to performing the SRB assay. In the second set, the cells from 50 different cell lines (a subset of the first 56 cell lines, plus the renal cancer cell line 786–0) were exposed continuously for six days prior to the SRB assay.

TABLE 1

| | Time | Mean Optical Densities | | | | | | Log 10 Concentration Percent Growth | | | | | | | |
|---|---|---|---|---|---|---|---|---|---|---|---|---|---|---|---|
| | Zero | Ctrl | −8.9 | −7.9 | −6.9 | −5.9 | −4.9 | −8.9 | −7.9 | −6.9 | −5.9 | −4.9 | GI50 | TGI | LC50 |
| Leukemia | | | | | | | | | | | | | | | |
| CCRF-CEM | 0.300 | 1.155 | 1.203 | 1.195 | 1.134 | 0.704 | 0.285 | 106 | 105 | 98 | 47 | −5 | 1.11E−06 | 1.00E−05 | >1.26E−05 |
| HL-60(TB) | 0.233 | 0.530 | 0.533 | 0.507 | 0.335 | 0.499 | 0.213 | 101 | 92 | 102 | 90 | −9 | 3.19E−06 | 1.03E−05 | >1.26E−05 |
| K-562 | 0.209 | 1.416 | 1.387 | 1.431 | 1.418 | 1.124 | 0.199 | 98 | 101 | 100 | 76 | −5 | 2.63E−06 | 1.10E−05 | >1.26E−05 |
| MOLT-4 | 0.134 | 0.438 | 0.465 | 0.454 | 0.454 | 0.368 | 0.146 | 109 | 105 | 105 | 77 | 4 | 2.96E−06 | >1.26E−05 | >1.26E−05 |
| RPMI-8226 | 0.257 | 0.893 | 0.868 | 0.848 | 0.813 | 0.670 | 0.204 | 96 | 93 | 87 | 65 | −21 | 1.88E−06 | 7.23E−06 | >1.26E−05 |
| SR | 0.158 | 0.457 | 0.454 | 0.425 | 0.457 | 0.338 | 0.111 | 99 | 89 | 100 | 60 | −30 | 1.63E−06 | 5.85E−06 | >1.26E−05 |
| Non-Small Cell Lung Cancer | | | | | | | | | | | | | | | |
| A549/ATCC | 0.015 | 0.477 | 0.479 | 0.486 | 0.476 | 0.516 | 0.336 | 100 | 102 | 100 | 108 | 69 | >1.26E−05 | >1.26E−05 | >1.26E−05 |
| EKVX | 0.342 | 0.736 | 0.809 | 0.849 | 0.841 | 0.853 | 0.385 | 119 | 129 | 127 | 130 | 11 | 5.91E−06 | >1.26E−05 | >1.26E−05 |
| HOP-62 | 0.335 | 1.109 | 1.088 | 1.099 | 1.113 | 1.086 | 0.605 | 97 | 99 | 100 | 97 | 35 | 7.18E−06 | >1.26E−05 | >1.26E−05 |
| HOP-92 | 0.505 | 1.694 | 1.554 | 1.603 | 1.477 | 1.381 | 0.873 | 88 | 92 | 82 | 74 | 31 | 4.50E−06 | >1.26E−05 | >1.26E−05 |
| NCI-H226 | 0.560 | 0.932 | 0.967 | 0.918 | 0.967 | 0.967 | 0.904 | 109 | 96 | 109 | 109 | 92 | >1.26E−05 | >1.26E−05 | >1.26E−05 |
| NCI-H23 | 0.648 | 1.622 | 1.769 | 1.822 | 1.880 | 1.635 | 1.215 | 115 | 121 | 127 | 101 | 58 | >1.26E−05 | >1.26E−05 | >1.26E−05 |
| NCI-8322M | 0.382 | 0.997 | 1.103 | 1.036 | 0.976 | 0.992 | 0.755 | 117 | 106 | 97 | 99 | 61 | >1.26E−05 | >1.26E−05 | >1.26E−05 |
| NCI-H460 | 0.296 | 1.235 | 1.132 | 1.186 | 1.234 | 1.157 | 0.757 | 89 | 95 | 100 | 92 | 49 | 1.20E−05 | >1.26E−05 | >1.26E−05 |
| NCI-H522 | 0.478 | 1.138 | 1.332 | 1.135 | 1.189 | 0.892 | 0.378 | 129 | 100 | 108 | 63 | −21 | 1.79E−06 | 7.08E−06 | >1.26E−05 |
| Colon Cancer | | | | | | | | | | | | | | | |
| COLO 205 | 0.328 | 1.394 | 1.425 | 1.414 | 1.576 | 1.434 | 0.935 | 103 | 102 | 117 | 104 | 57 | >1.26E−05 | >1.26E−05 | >1.26E−05 |
| HCT-116 | 0.301 | 1.574 | 1.508 | 1.480 | 1.488 | 1.391 | 0.685 | 95 | 93 | 93 | 86 | 30 | 5.53E−06 | >1.26E−05 | >1.26E−05 |
| HCT-15 | 0.219 | 1.623 | 1.800 | 1.627 | 1.673 | 1.522 | 0.504 | 113 | 100 | 104 | 93 | 20 | 4.90E−06 | >1.26E−05 | >1.26E−05 |
| HT29 | 0.095 | 0.578 | 0.637 | 0.599 | 0.580 | 0.479 | 0.169 | 112 | 104 | 100 | 80 | 15 | 3.63E−06 | >1.26E−05 | >1.26E−05 |
| KM12 | 0.189 | 0.741 | 0.744 | 0.728 | 0.777 | 0.737 | 0.567 | 101 | 98 | 106 | 99 | 68 | >1.26E−05 | >1.26E−05 | >1.26E−05 |
| SW-620 | 0.153 | 0.886 | 0.898 | 0.868 | 0.857 | 0.779 | 0.267 | 102 | 98 | 96 | 85 | 16 | 4.05E−06 | >1.26E−05 | >1.26E−05 |
| CNS Cancer | | | | | | | | | | | | | | | |
| SF-268 | 0.203 | 0.767 | 0.821 | 0.736 | 0.815 | 0.767 | 0.334 | 110 | 94 | 108 | 100 | 23 | 5.63E−06 | >1.26E−05 | >1.26E−05 |
| SF-295 | 0.249 | 1.007 | 0.951 | 0.978 | 0.938 | 0.938 | 0.639 | 93 | 96 | 91 | 91 | 51 | >1.26E−05 | >1.26E−05 | >1.26E−05 |
| SF-539 | 0.132 | 0.462 | 0.491 | 0.516 | 0.506 | 0.435 | 0.110 | 109 | 117 | 113 | 92 | −17 | 3.06E−06 | 8.85E−06 | >1.26E−05 |
| SNB-19 | 0.176 | 0.905 | 0.857 | 0.880 | 0.887 | 0.883 | 0.437 | 93 | 97 | 98 | 97 | 36 | 7.38E−06 | >1.26E−05 | >1.26E−05 |
| SNB-75 | 0.501 | 1.051 | 0.925 | 1.049 | 1.134 | 0.703 | 0.438 | 77 | 100 | 115 | 37 | −17 | 8.54E−07 | 6.98E−06 | >1.26E−05 |
| U251 | 0.192 | 0.799 | 0.789 | 0.792 | 0.803 | 0.680 | 0.061 | 98 | 99 | 101 | 80 | −68 | 2.02E−06 | 4.37E−06 | 9.47E−06 |

TABLE 1-continued

| | Time | | Mean Optical Densities | | | | | Percent Growth | | | | | | | |
|---|---|---|---|---|---|---|---|---|---|---|---|---|---|---|---|
| | | | | | Log 10 Concentration | | | | | | | | | | |
| | Zero | Ctrl | −8.9 | −7.9 | −6.9 | −5.9 | −4.9 | −8.9 | −7.9 | −6.9 | −5.9 | −4.9 | GI50 | TGI | LC50 |
| Melanoma | | | | | | | | | | | | | | | |
| LOX IMVI | 0.173 | 1.304 | 1.175 | 1.170 | 0.974 | 0.997 | 0.319 | 89 | 88 | 71 | 73 | 13 | 3.03E−06 | >1.26E−05 | >1.26E−05 |
| MALME-3M | 0.476 | 0.859 | 1.006 | 0.949 | 0.868 | 0.819 | 0.275 | 138 | 123 | 102 | 90 | −42 | 2.51E−06 | 6.02E−06 | >1.26E−05 |
| M14 | 0.123 | 0.613 | 0.602 | 0.635 | 0.592 | 0.549 | 0.136 | 98 | 105 | 96 | 87 | 3 | 3.45E−06 | >1.26E−05 | >1.26E−05 |
| SK-MEL-2 | 0.388 | 0.704 | 0.746 | 0.714 | 0.735 | 0.676 | 0.323 | 113 | 103 | 110 | 91 | −17 | 3.03E−06 | 8.81E−06 | >1.26E−05 |
| SK-MEL-28 | 0.513 | 1.090 | 1.088 | 1.107 | 1.093 | 1.057 | 0.546 | 100 | 103 | 101 | 94 | 6 | 3.98E−06 | >1.26E−05 | >1.26E−05 |
| SK-MEL-5 | 0.454 | 2.107 | 2.049 | 2.066 | 2.025 | 1.748 | 0.460 | 96 | 97 | 95 | 78 | 0 | 2.90E−06 | >1.26E−05 | >1.26E−05 |
| UACC-257 | 0.596 | 1.142 | 1.149 | 1.128 | 1.165 | 1.078 | 0.814 | 101 | 97 | 104 | 88 | 40 | 7.78E−06 | >1.26E−05 | >1.26E−05 |
| UACC-62 | 0.306 | 1.082 | 1.111 | 1.105 | 1.108 | 1.051 | 0.355 | 104 | 103 | 103 | 96 | 6 | 4.10E−06 | >1.26E−05 | >1.26E−05 |
| Ovarian Cancer | | | | | | | | | | | | | | | |
| IGROV1 | 0.291 | 1.679 | 1.828 | 1.932 | 1.743 | 1.710 | 0.536 | 111 | 118 | 105 | 102 | 18 | 5.22E−06 | >1.26E−05 | >1.26E−05 |
| OVCAR-3 | 0.240 | 1.066 | 1.073 | 1.055 | 1.045 | 0.980 | 0.343 | 101 | 99 | 97 | 90 | 12 | 4.10E−06 | >1.26E−05 | >1.26E−05 |
| OVCAR-5 | 0.457 | 1.206 | 1.243 | 1.230 | 1.157 | 1.181 | 0.715 | 105 | 103 | 93 | 97 | 34 | 7.07E−06 | >1.26E−05 | >1.26E−05 |
| OVCAR-8 | 0.173 | 1.340 | 1.250 | 1.245 | 1.159 | 1.107 | 0.495 | 92 | 92 | 84 | 80 | 28 | 4.71E−06 | >1.26E−05 | >1.26E−05 |
| SK-OV-3 | 0.351 | 0.865 | 0.836 | 0.852 | 0.853 | 0.867 | 0.557 | 94 | 97 | 98 | 100 | 40 | 8.59E−06 | >1.26E−05 | >1.26E−05 |
| Renal Cancer | | | | | | | | | | | | | | | |
| A498 | 0.400 | 0.678 | 0.691 | 0.657 | 0.649 | 0.635 | 0.357 | 105 | 93 | 89 | 84 | −11 | 2.90E−06 | 9.71E−06 | >1.26E−05 |
| CAKI-1 | 0.372 | 0.942 | 1.058 | 0.960 | 1.103 | 0.819 | 0.325 | 120 | 103 | 128 | 78 | −13 | 2.59E−06 | 9.13E−06 | >1.26E−05 |
| RXE 393 | 0.743 | 1.243 | 0.860 | 1.114 | 1.290 | 1.077 | 0.776 | 23 | 74 | 109 | 67 | 7 | . | >1.26E−05 | >1.26E−05 |
| SN12C | 0.157 | 0.546 | 0.533 | 0.529 | 0.500 | 0.474 | 0.113 | 97 | 96 | 88 | 81 | −28 | 2.44E−06 | 6.96E−06 | >1.26E−05 |
| TX-10 | 0.355 | 1.027 | 1.014 | 1.002 | 1.042 | 0.999 | 0.727 | 98 | 96 | 102 | 96 | 55 | >1.26E−05 | >1.26E−05 | >1.26E−05 |
| UO-31 | 0.124 | 0.765 | 0.799 | 0.816 | 0.830 | 0.785 | 0.391 | 105 | 108 | 110 | 103 | 42 | 9.20E−06 | >1.26E−05 | >1.26E−05 |
| Prostate Cancer | | | | | | | | | | | | | | | |
| PC-3 | 0.187 | 0.419 | 0.426 | 0.399 | 0.390 | 0.342 | 0.179 | 103 | 91 | 88 | 67 | −4 | 2.17E−06 | 1.10E−05 | >1.26E−05 |
| DU-145 | 0.384 | 1.151 | 1.081 | 1.389 | 1.194 | 1.119 | 0.873 | 91 | 131 | 106 | 96 | 64 | >1.26E−05 | >1.26E−05 | >1.26E−05 |
| Breast Cancer | | | | | | | | | | | | | | | |
| MCF7 | 0.200 | 0.928 | 0.924 | 0.912 | 0.985 | 0.893 | 0.277 | 99 | 98 | 108 | 95 | 11 | 4.31E−06 | >1.26E−05 | >1.26E−05 |
| NCI/ADR-RES | 0.328 | 1.386 | 1.576 | 1.376 | 1.425 | 1.298 | 0.801 | 118 | 99 | 104 | 92 | 45 | 9.69E−06 | >1.26E−05 | >1.26E−05 |
| MDA-MB-231/ATCC | 0.304 | 0.644 | 0.635 | 0.651 | 0.674 | 0.667 | 0.314 | 97 | 102 | 109 | 107 | 3 | 4.43E−06 | >1.26E−05 | >1.26E−05 |
| HS 578T | 0.369 | 1.255 | 1.338 | 1.296 | 1.219 | 1.300 | 0.742 | 109 | 105 | 96 | 105 | 42 | 9.44E−06 | >1.26E−05 | >1.26E−05 |
| MDA-MB-435 | 0.465 | 1.425 | 1.370 | 1.354 | 1.476 | 1.369 | 0.666 | 94 | 93 | 105 | 94 | 21 | 5.05E−06 | >1.26E−05 | >1.26E−05 |
| MDA-N | 0.348 | 1.471 | 1.499 | 1.481 | 1.374 | 1.316 | 0.385 | 102 | 101 | 91 | 86 | 3 | 3.44E−06 | >1.26E−05 | >1.26E−05 |
| BT-549 | 0.735 | 1.762 | 1.910 | 1.865 | 1.847 | 1.599 | 0.998 | 114 | 110 | 108 | 84 | 26 | 4.82E−06 | >1.26E−05 | >1.26E−05 |
| T-47D | 0.464 | 1.007 | 0.941 | 1.054 | 1.184 | 0.905 | 0.419 | 88 | 109 | 133 | 81 | −10 | 2.78E−06 | 9.86E−06 | >1.26E−05 |

Figure 2A:
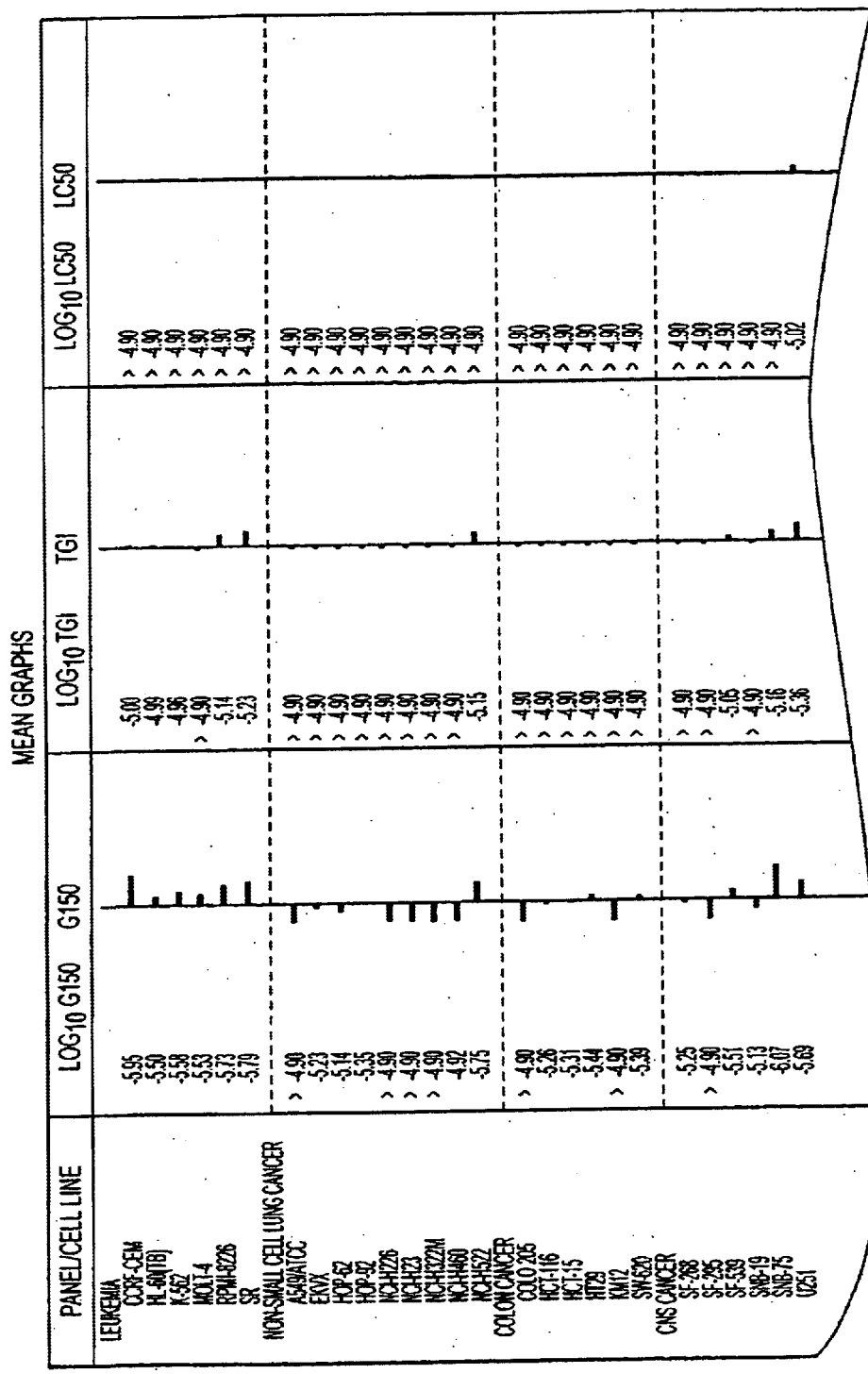
FIG. 2. Mean graphs showing selectivity patterns at each of the principal response parameters for all the cell lines tested after continous exposure to $10^{-5}$ to $10^{-9}$ μg/ml of arsenic trioxide for 2 days.
Figure 2B:
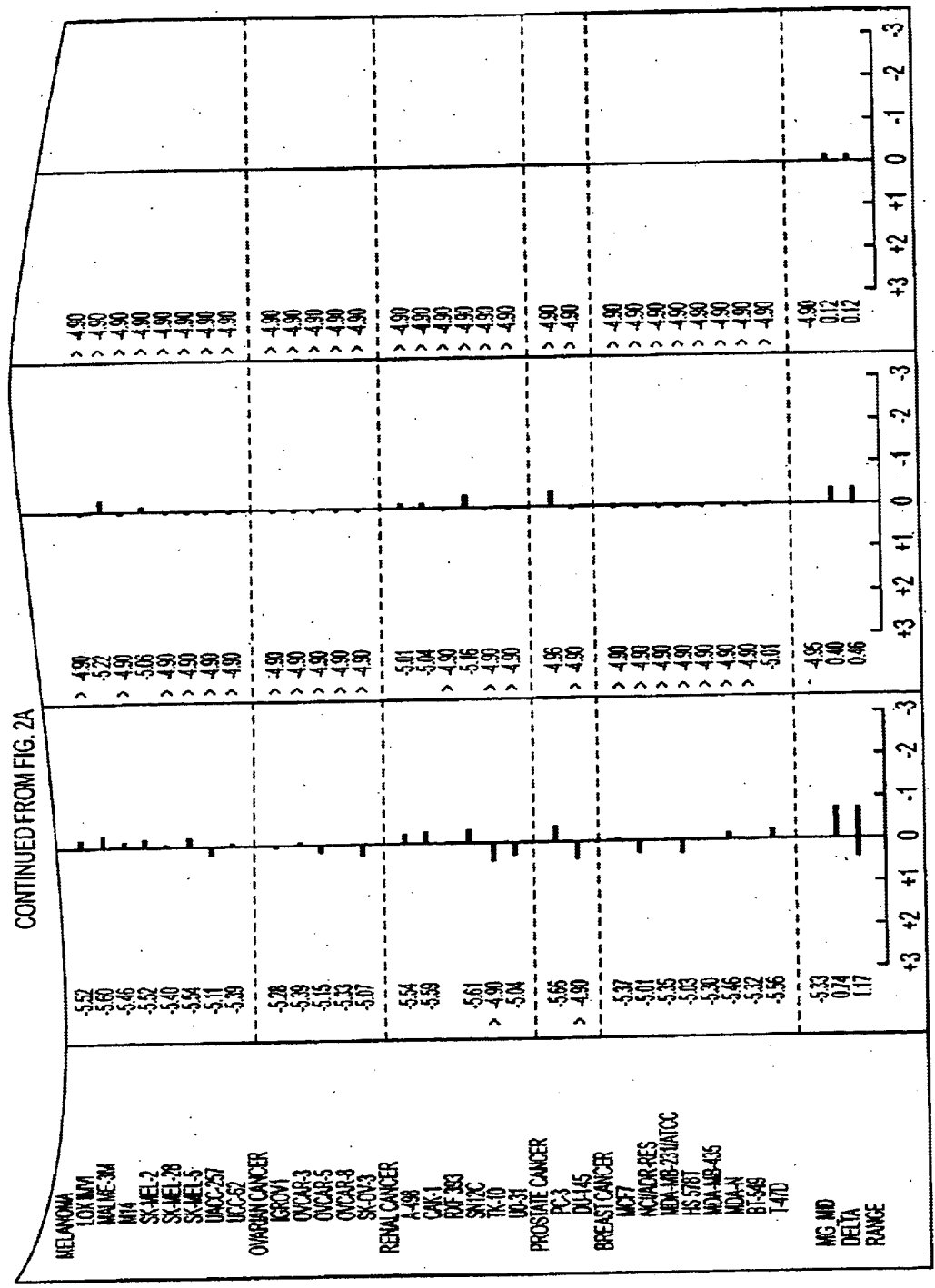
Figure 3A:
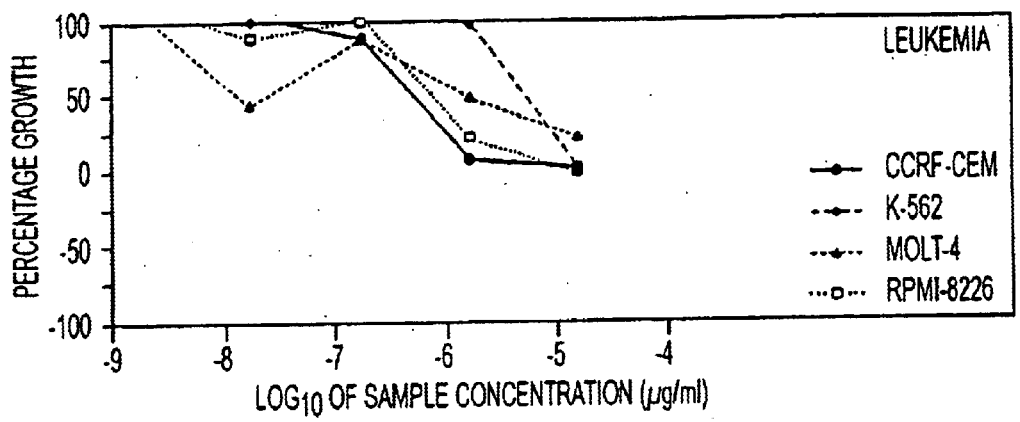
FIGS. 3A–3I. Dose response curves showing percentage growth of various cancer cell lines after continuous exposure to $10^{-5}$ to $10^{-9}$ μg/ml cf arsenic trioxide for 6 days.
Figure 3B:
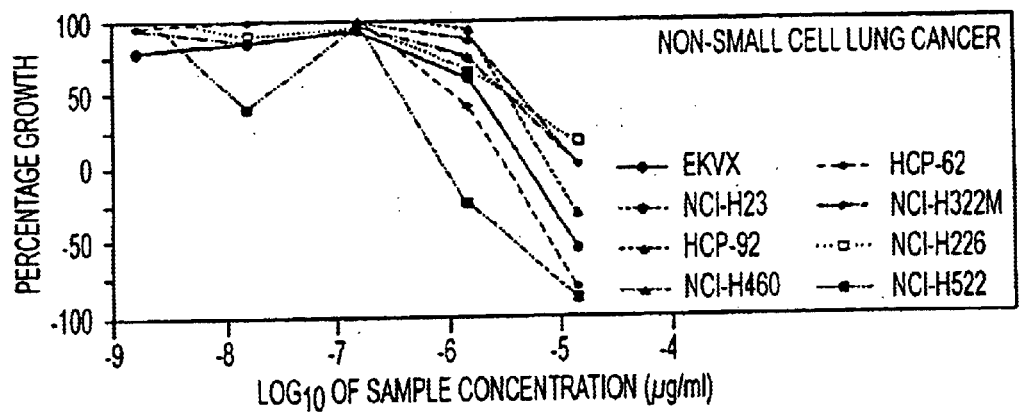
Figure 3C:
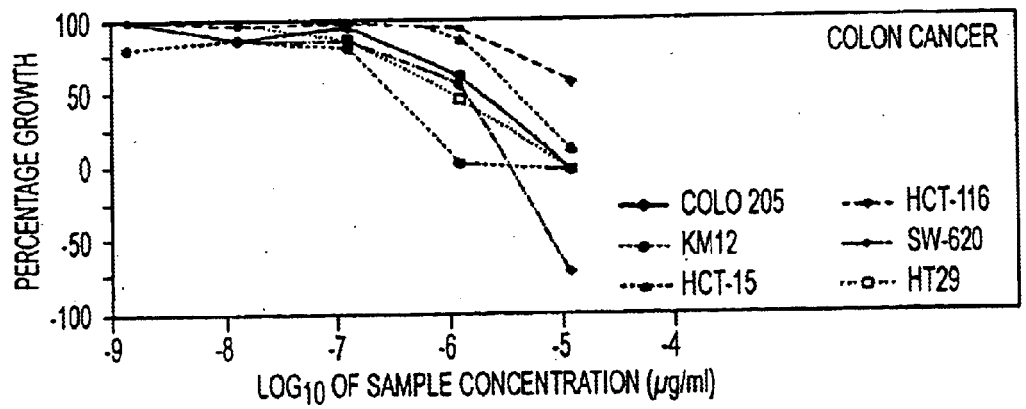
Figure 3D:
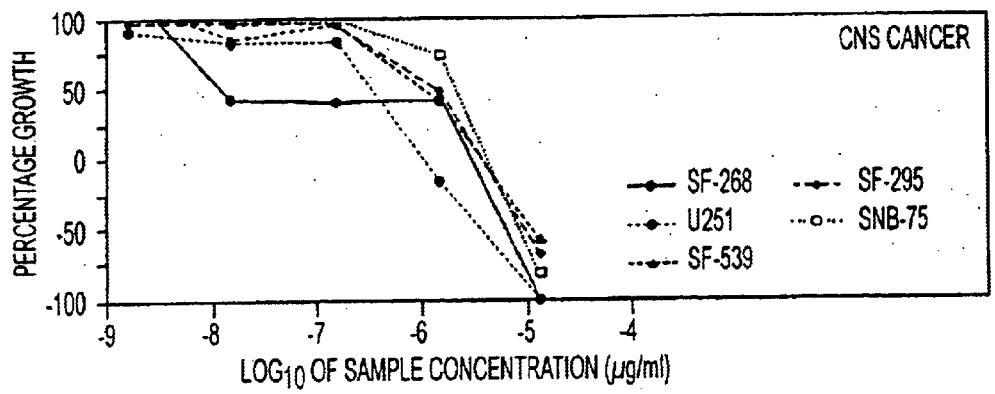
Figure 3E:
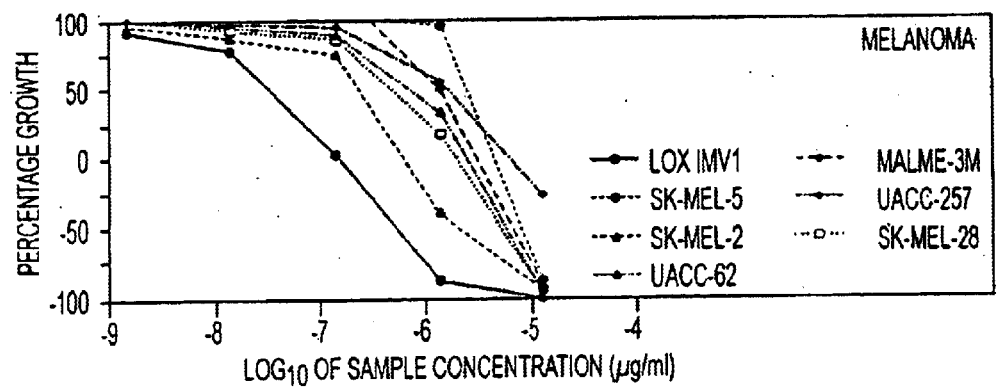
Figure 3F:
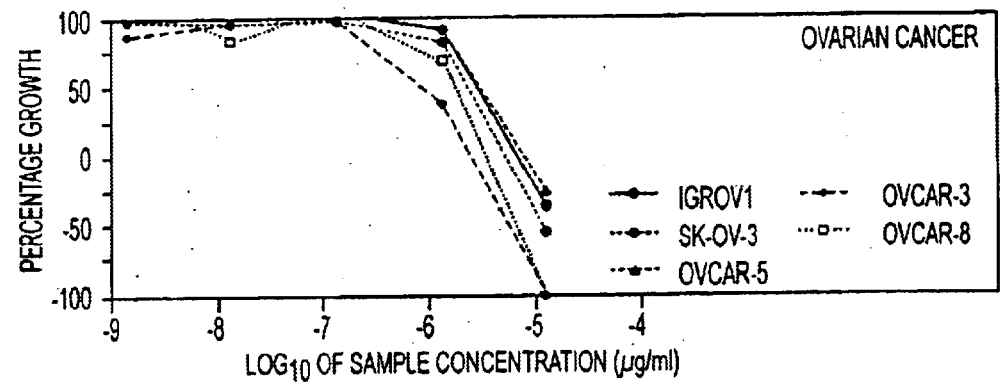
Figure 3G:
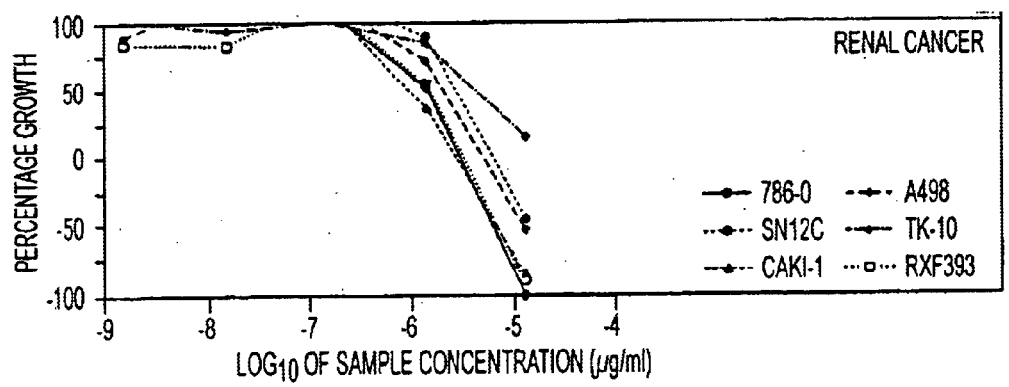
Figure 3H:
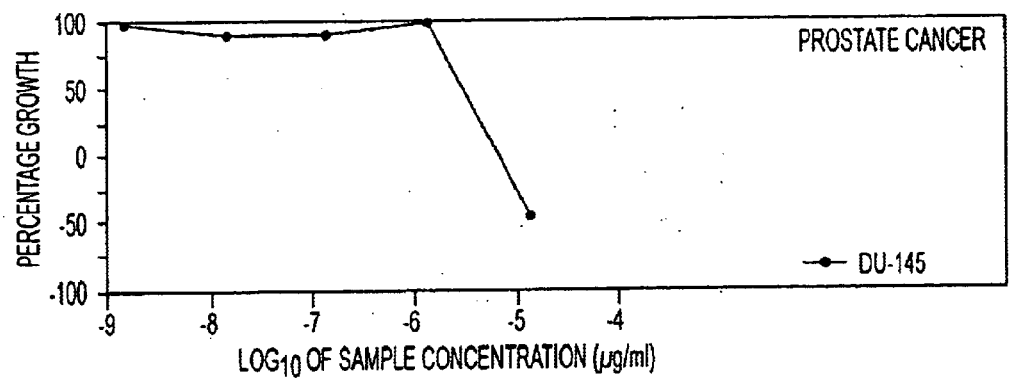
Figure 3I:
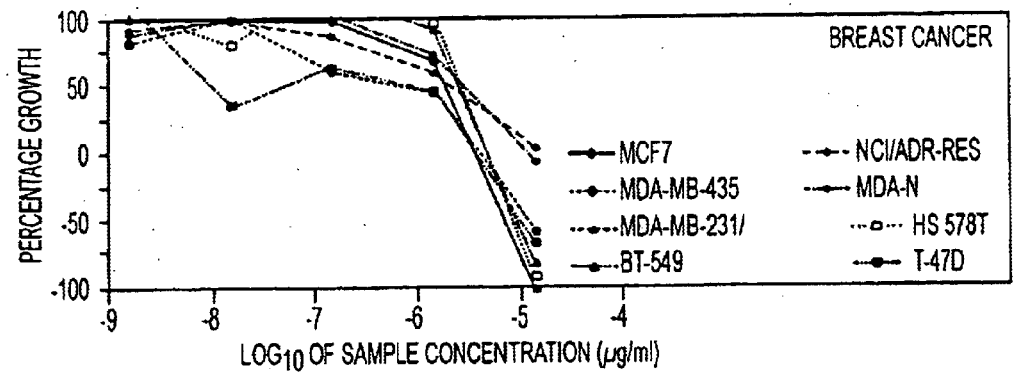

In the first set of tests, according to Table 1 and the dose response curves as shown in FIGS. 1A to 1I, arsenic trioxide was effective in reducing cell growth against almost all the cell lines tested. In particular, leukemic cell lines, melanoma cell lines, and ovarian cancer cell lines responded consistently by showing a reduction of more than 50% growth. According to the mean graph as shown in FIG. 2, most of the leukemic and melanoma cell lines, central nervous system cancer cell lines SNB-75 and U251, prostate cancer cell line PC-3, renal cancer cell lines A498, CAKI-1, SN12C, and lung cancer cell line, NCI-H522 were especially sensitive (relative to all the cell lines tested) to treatment with arsenic trioxide.

TABLE 2

| | Time | | Mean Optical Densities | | | | | Percent Growth | | | | | | | |
|---|---|---|---|---|---|---|---|---|---|---|---|---|---|---|---|
| | | | | | Log 10 Concentration | | | | | | | | | | |
| | Zero | Ctrl | −8.9 | −7.9 | −6.9 | −5.9 | −4.9 | −8.9 | −7.9 | −6.9 | −5.9 | −4.9 | GI50 | TGI | LC50 |
| Panel/Cell Line | | | | | | | | | | | | | | | |
| Leukemia | | | | | | | | | | | | | | | |
| CCRF-CEM | 0.047 | 3.511 | 3.601 | 3.592 | 3.051 | 0.320 | 0.048 | 103 | 102 | 87 | 8 | 0 | 3.68E−07 | >1.26E−05 | >1.26E−05 |
| K-562 | 0.041 | 3.011 | 3.042 | 2.992 | 3.360 | 2.931 | 0.096 | 101 | 99 | 112 | 97 | 2 | 3.941−06 | >1.26E−05 | >1.26E−05 |
| MOLT-4 | 0.018 | 0.503 | 0.554 | 0.228 | 0.432 | 0.245 | 0.113 | 111 | 43 | 85 | 47 | 20 | . | >1.26E−05 | >1.26E−05 |
| RPMI-8226 | 0.066 | 1.432 | 1.607 | 1.263 | 1.423 | 0.368 | 0.065 | 113 | 88 | 99 | 22 | −2 | 5.481−07 | 1.091−05 | >1.26E−05 |

TABLE 2-continued

| | Time | Mean Optical Densities | | | | | | Percent Growth | | | | | | | |
|---|---|---|---|---|---|---|---|---|---|---|---|---|---|---|---|
| | | | | | Log 10 Concentration | | | | | | | | | | |
| | Zero | Ctrl | −8.9 | −7.9 | −6.9 | −5.9 | −4.9 | −8.9 | −7.9 | −6.9 | −5.9 | −4.9 | GI50 | TGI | LC50 |
| Non-small Cell Lung Cancer | | | | | | | | | | | | | | | |
| EKVX | 0.030 | 0.682 | 0.573 | 0.601 | 0.628 | 0.414 | 0.014 | 83 | 88 | 92 | 59 | −53 | 1.51E−06 | 4.22E−06 | 1.18E−05 |
| HOP-62 | 0.061 | 1.026 | 1.076 | 0.997 | 1.019 | 0.451 | 0.014 | 105 | 97 | 99 | 40 | −77 | 8.66E−07 | 2.78I−06 | 7.41E−06 |
| HOP-92 | 0.115 | 1.292 | 1.455 | 1.834 | 1.319 | 1.229 | 0.079 | 114 | 146 | 102 | 95 | −31 | 2.85E−06 | 7.11I−06 | >1.26E−05 |
| NCI-H226 | 0.094 | 0.498 | 0.504 | 0.458 | 0.489 | 0.348 | 0.164 | 101 | 90 | 98 | 63 | 17 | 2.40E−08 | >1.26I−05 | >1.26E−05 |
| NCI-H23 | 0.075 | 1.624 | 1.818 | 1.814 | 1.872 | 1.303 | 0.086 | 113 | 112 | 116 | 79 | 1 | 2.97E−06 | >1.26I−05 | >1.26E−05 |
| NCI-H322M | 0.035 | 0.702 | 0.680 | 0.620 | 0.674 | 0.552 | 0.054 | 97 | 88 | 96 | 77 | 3 | 2.94E−06 | >1.26I−05 | >1.26E−05 |
| NCI-H460 | 0.034 | 2.839 | 2.797 | 2.806 | 2.792 | 2.535 | 0.062 | 99 | 99 | 98 | 89 | 1 | 3.50E−06 | >1.26I−05 | >1.26E−05 |
| NCI-H522 | 0.175 | 1.224 | 1.269 | 0.535 | 1.191 | 0.128 | 0.028 | 104 | 34 | 97 | −27 | −84 | . | 7.64I−07 | 3.19E−06 |
| Colon Cancer | | | | | | | | | | | | | | | |
| COLO 205 | 0.022 | 2.351 | 2.308 | 2.026 | 2.283 | 1.404 | 0.024 | 98 | 86 | 97 | 59 | 0 | 1.81E−06 | >1.26E−05 | >1.26E−05 |
| HCT-116 | 0.046 | 3.420 | 3.395 | 3.289 | 3.381 | 3.284 | 1.931 | 99 | 96 | 99 | 96 | 56 | >1.26E−05 | >1.26E−05 | >1.26E−05 |
| HCT-15 | 0.033 | 3.838 | 3.965 | 3.921 | 4.227 | 3.432 | 0.404 | 103 | 102 | 110 | 89 | 10 | 3.93E−06 | >1.26E−05 | >1.26E−05 |
| HT29 | 0.017 | 3.060 | 3.189 | 2.988 | 2.706 | 1.476 | 0.027 | 104 | 98 | 88 | 48 | 0 | 1.12E−06 | >1.26E−05 | >1.26E−05 |
| KM12 | 0.012 | 0.808 | 0.487 | 0.533 | 0.507 | 0.036 | 0.017 | 80 | 87 | 83 | 4 | 1 | 3.29E−07 | >1.26E−05 | >1.26E−05 |
| SW-620 | 0.023 | 2.652 | 2.613 | 2.308 | 2.337 | 1.475 | 0.007 | 99 | 87 | 88 | 55 | −72 | 1.39E−06 | 3.43E−06 | 8.50E−06 |
| CNS Cancer | | | | | | | | | | | | | | | |
| SF-268 | 0.054 | 0.798 | 0.990 | 0.381 | 0.356 | 0.387 | −0.004 | 126 | 44 | 41 | 45 | −100 | 1.06E−08 | 2.57E−06 | 5.69E−06 |
| SF-295 | 0.031 | 1.324 | 1.284 | 1.279 | 1.244 | 0.659 | 0.010 | 97 | 97 | 94 | 49 | −69 | 1.17E−06 | 3.25E−06 | 8.64E−06 |
| SF-539 | 0.041 | 1.598 | 1.727 | 1.403 | 1.545 | 0.691 | 0.017 | 108 | 87 | 97 | 42 | −59 | 8.91E−07 | 3.29E−06 | 1.04E−05 |
| SNB-75 | 0.134 | 1.065 | 1.143 | 1.033 | 1.024 | 0.815 | 0.028 | 108 | 97 | 96 | 73 | −79 | 1.79E−06 | 3.80E−06 | 8.08E−06 |
| U251 | 0.105 | 2.324 | 2.129 | 2.018 | 1.908 | 0.088 | −0.012 | 91 | 86 | 81 | −17 | −100 | 2.63E−07 | 8.51E−07 | 3.16E−06 |
| Melanoma | | | | | | | | | | | | | | | |
| LOX 1MVI | 0.013 | 2.153 | 2.000 | 1.666 | 0.053 | 0.002 | −0.001 | 93 | 77 | 2 | −88 | −100 | 2.90E−08 | 1.32E−07 | 4.73E−07 |
| MALMI-3M | 0.115 | 0.650 | 0.702 | 0.595 | 0.823 | 0.383 | 0.005 | 110 | 90 | 132 | 50 | −96 | 1.26E−06 | 2.78E−06 | 6.12E−06 |
| SK-MEL-2 | 0.213 | 0.500 | 0.491 | 0.462 | 0.426 | 0.128 | . | 97 | 87 | 74 | −40 | −100 | 2.06E−07 | 5.63E−07 | 1.85E−06 |
| SK-MEL-28 | 0.093 | 2.030 | 2.012 | 1.906 | 1.797 | 0.488 | . | 99 | 94 | 88 | 20 | −100 | 4.60E−07 | 1.86E−06 | 4.84E−06 |
| SK-MEL-5 | 0.181 | 1.907 | 1.935 | 1.864 | 1.929 | 1.846 | 0.013 | 102 | 97 | 101 | 96 | −93 | 2.22E−06 | 4.07E−06 | 7.46E−06 |
| UACC-257 | 0.053 | 0.883 | 0.872 | 0.857 | 0.832 | 0.504 | 0.039 | 99 | 97 | 94 | 54 | −27 | 1.42E−06 | 5.83E−06 | >1.26E−05 |
| UACC-62 | 0.030 | 1.537 | 1.546 | 1.460 | 1.409 | 0.539 | 0.001 | 101 | 95 | 92 | 34 | −98 | 6.60E−07 | 2.27E−06 | 5.43E−06 |
| Ovarian Cancer | | | | | | | | | | | | | | | |
| IGROV1 | 0.335 | 3.115 | 3.541 | 3.056 | 3.204 | 2.877 | 0.216 | 115 | 98 | 103 | 91 | −36 | 2.67E−06 | 6.62E−06 | >1.26E−05 |
| OVCAR-3 | 0.081 | 1.153 | 1.047 | 1.128 | 1.124 | 0.482 | 0.001 | 90 | 98 | 97 | 37 | −99 | 7.76E−07 | 2.36E−06 | 5.49E−06 |
| OVCAR-5 | 0.038 | 1.404 | 1.433 | 1.460 | 1.478 | 1.287 | 0.003 | 102 | 104 | 105 | 91 | −26 | 2.83E−06 | 7.53E−06 | >1.26E−05 |
| OVCAR-8 | 0.016 | 2.090 | 2.272 | 1.848 | 2.242 | 1.437 | −0.001 | 109 | 88 | 107 | 68 | −100 | 1.62E−06 | 3.21E−06 | 6.36E−06 |
| SK-OV-3 | 0.041 | 1.474 | 1.445 | 1.410 | 1.461 | 1.247 | 0.020 | 98 | 96 | 99 | 84 | −51 | 2.25E−06 | 5.27E−06 | 1.23E−05 |
| Renal Cancer | | | | | | | | | | | | | | | |
| 786-0 | 0.021 | 1.578 | 1.582 | 1.821 | 1.786 | 0.832 | −0.003 | 100 | 116 | 113 | 52 | −100 | 1.30E−06 | 2.77E−06 | 5.91E−06 |
| A498 | 0.051 | 0.741 | 0.826 | 0.764 | 0.837 | 0.558 | 0.025 | 112 | 103 | 114 | 73 | −52 | 1.94E−06 | 4.85E−06 | 1.22E−05 |
| CAKI-1 | 0.032 | 1.352 | 1.254 | 1.725 | 1.573 | 0.491 | 0.004 | 93 | 128 | 117 | 35 | −88 | 8.22E−07 | 2.43E−06 | 6.22E−06 |
| RXF393 | 0.198 | 1.515 | 1.327 | 1.301 | 1.727 | 0.909 | 0.017 | 86 | 84 | 116 | 54 | −91 | 1.34E−06 | 2.96E−06 | 6.54E−06 |
| S12C | 0.024 | 0.956 | 0.882 | 1.141 | 1.113 | 0.829 | 0.013 | 92 | 120 | 117 | 86 | −46 | 2.37E−06 | 5.67E−06 | >1.26E−05 |
| TK-10 | 0.072 | 1.333 | 1.356 | 1.268 | 1.334 | 1.103 | 0.239 | 102 | 95 | 100 | 82 | 13 | 3.66E−06 | >1.26E−05 | >1.26E−05 |
| Prostate Cancer | | | | | | | | | | | | | | | |
| DU-145 | 0.095 | 2.158 | 2.147 | 1.954 | 1.935 | 2.153 | 0.055 | 99 | 90 | 89 | 100 | −43 | 2.82E−06 | 6.32E−06 | >1.26E−05 |
| Breast Cancer | | | | | | | | | | | | | | | |
| MCF7 | 0.028 | 2.650 | 2.647 | 2.611 | 2.603 | 1.683 | 0.008 | 100 | 99 | 98 | 63 | −73 | 1.57E−06 | 3.66E−06 | 8.51E−06 |
| NCI/ADR-RIS | 0.050 | 2.304 | 2.075 | 2.253 | 1.951 | 1.319 | 0.072 | 90 | 98 | 84 | 56 | 1 | 1.64E−06 | >1.26E−05 | >1.26E−05 |
| MDA-MB-231/ATCC | 0.158 | 0.761 | 0.759 | 0.764 | 0.771 | 0.563 | −0.001 | 100 | 101 | 102 | 67 | −100 | 1.59E−06 | 3.18E−06 | 6.33E−06 |
| HS 578T | 0.109 | 0.728 | 0.777 | 0.587 | 0.890 | 0.706 | 0.010 | 108 | 77 | 126 | 96 | −91 | 2.23E−06 | 4.12E−06 | 7.62E−06 |
| MDA-MB-435 | 0.054 | 1.500 | 1.276 | 1.470 | 0.865 | 0.631 | 0.021 | 85 | 98 | 56 | 40 | −62 | 3.00E−07 | 3.10E−06 | 9.60E−06 |
| MDA-N | 0.028 | 2.652 | 2.468 | 2.616 | 2.606 | 1.738 | 0.026 | 93 | 99 | 98 | 65 | −9 | 2.02E−06 | 9.55E−06 | >1.26E−05 |
| BT-549 | 0.112 | 1.798 | 1.876 | 1.940 | 1.963 | 1.697 | 0.018 | 105 | 108 | 110 | 94 | −84 | 2.22E−06 | 4.24E−06 | 8.08E−06 |
| T-47D | 0.098 | 0.824 | 0.883 | 0.336 | 0.539 | 0.398 | 0.027 | 108 | 33 | 61 | 41 | −73 | . | 2.90E−06 | 7.93E−06 |

In the second set of tests, according to Table 2, the dose response curves, and the mean graph as shown in FIGS. 3A to 3I, and FIG. 4, arsenic trioxide was effective in reducing cell growth against all the cell lines tested. The results were consistent with those obtained from the first set of tests. In particular, several melanoma cell lines appeared to be especially sensitive at the various principal response parameters.

In conclusion, these results demonstrate that arsenic trioxide is effective in inhibiting the growth of leukemic cells and cancer cells in vitro, and that arsenic trioxide can be used in human subjects to treat a broad range of leukemia, and cancers, including but not limited to non-small cell lung cancer, colon cancer, central nervous system cancer, melanoma, ovarian cancer, renal cancer, prostate cancer, and breast cancer The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of treatment of solid tumors in a human, which comprises administering to a human in need of said treatment a therapeutically effective amount of arsenic trioxide, wherein said solid tumor is a tumor of the central nervous system that is selected from the group consisting of neuroblastoma, retinoblastoma, glioblastoma, and oligodendroglioma.

2. The method of claim 1, wherein said solid tumor is a metastatic tumor.

3. The method of claim 1 or 2 wherein said arsenic compound is administered in combination with a therapeutically effective amount of at least one other therapeutic agent.

4. The method of claim 1 or 2 wherein the total daily amount administered is from about 10 µg to about 200 mg.

5. The method of claim 3, in which said at least one other therapeutic agent is a chemotherapeutic agent or radiotherapeutic agent.

6. The method of claims 1 or 2, in which said administration is made parenterally, topically, dermally, directly into the tumor or orally.

7. The method of claim 3, in which said at least one other therapeutic agent is selected from the group containing of etoposide, cisplatin, carboplatin, estramustine phosphate, vinblastine, methotrexate, hydroxyurea, cyclophosphamide, doxorubicin, 5-fluorouracil, taxol, diethylstilbestrol, VM-26 (vumon), BCNU, all-trans retinoic acid, procarbazine, cytokines, therapeutic vaccines, and mixtures thereof.

8. The method of claim 1 or 2, in which said administration is made via an implantation device.

9. The method of claim 1, wherein said arsenic trioxide is administered intravenously in a total daily dose of from 0.5 mg to 150 mg.

10. The method of claim 1 or 2, wherein the arsenic trioxide is administered orally.

11. The method of claim 1 or 2, wherein the arsenic trioxide is administered as a pill or tablet.

* * * * *